United States Patent [19]

Gargan

[11] Patent Number: 5,843,690

[45] Date of Patent: *Dec. 1, 1998

[54] IMMUNOASSAY AND KIT FOR IN VITRO DETECTION OF SOLUBLE DESAABB FIBRIN POLYMERS

[75] Inventor: Paul E. Gargan, Southbend, Ind.

[73] Assignee: American Biogenetic Sciences, Inc., Copiague, N.Y.

[ * ] Notice: The term of this patent shall not extend beyond the expiration date of Pat. No. 5,453,359.

[21] Appl. No.: 459,596

[22] Filed: Jun. 2, 1995

Related U.S. Application Data

[60] Division of Ser. No. 86,423, Jul. 2, 1993, Pat. No. 5,453,359, which is a continuation-in-part of Ser. No. 81,914, Jun. 22, 1993, abandoned, which is a continuation of Ser. No. 835,800, Feb. 14, 1992, Pat. No. 5,223,410, which is a continuation of Ser. No. 364,053, Jun. 8, 1989, Pat. No. 5,120,834, which is a continuation-in-part of Ser. No. 206,259, Jun. 13, 1988, abandoned.

[51] Int. Cl.$^6$ ..................................................... C12Q 1/56
[52] U.S. Cl. .......................... 435/13; 435/7.92; 435/7.93; 435/7.94; 435/7.95; 435/962; 435/972; 435/975; 436/518; 436/548; 436/808; 530/388.25; 530/389.3
[58] Field of Search .................. 435/7.1, 7.9, 7.92–7.95, 435/13, 962, 972, 975; 436/518, 527, 530, 531, 548, 69, 808; 530/388.25, 389.3

[56] References Cited

U.S. PATENT DOCUMENTS

| | | |
|---|---|---|
| 3,912,805 | 10/1975 | Cayzer et al. . |
| 4,036,945 | 7/1977 | Haber . |
| 4,147,765 | 4/1979 | Stephan et al. . |
| 4,355,023 | 10/1982 | Ehrlich et al. . |
| 4,421,735 | 12/1983 | Haber et al. . |
| 4,438,209 | 3/1984 | Mosier ..................................... 436/542 |
| 4,550,086 | 10/1985 | Reinberz et al. ........................ 436/506 |
| 4,758,524 | 7/1988 | Bundesen et al. ....................... 436/548 |
| 4,916,070 | 4/1990 | Matsueda et al. .................... 435/172.2 |
| 4,927,916 | 5/1990 | Matsueda .............................. 530/387.1 |
| 5,091,512 | 2/1992 | Gargan et al. ........................ 530/387.1 |
| 5,120,834 | 6/1992 | Gargan et al. ...................... 530/388.25 |
| 5,223,410 | 6/1993 | Gargan et al. ........................ 435/70.21 |
| 5,453,359 | 9/1995 | Gargan et al. ............................. 435/13 |
| 5,487,892 | 1/1996 | Gargan ................................. 424/145.1 |

FOREIGN PATENT DOCUMENTS

| | | |
|---|---|---|
| 122478 | 10/1984 | European Pat. Off. . |
| 151239 | 8/1985 | European Pat. Off. . |
| 187658 | 7/1986 | European Pat. Off. . |
| 0347933 | 12/1989 | European Pat. Off. ................. 435/13 |
| WO 87/06263 | 10/1987 | WIPO . |

OTHER PUBLICATIONS

Cepica et al., "The use of ELISA for Detection of the Antibody–induced Conformational Change in a Virol Protein and its Intermolecular Spread," Journal of Virological Methods, 28 : 1–14, 1990.

Sher et al., "Two Ia. 17–Specific Monoclonal Antibodies Detect the Same Epitope but do not Share Idiotype," *The Journal of Immunology*, 133 (1): 338–344, 1984.

Addonizio et al., 1982, "Spect Imaging of Cardiac Transplant Rejection Using IN–111 Antimyosin Antibody", J. Nuclear Medicine 14(2):910; abstract No. 140.

Knight et al. 1986, "Evaluation of In–III Labeled Anti–Fibrin Antibody for Imaging Vascular Thrombi," Medicine 14(2): 975; abstract No. 402.

Bode et al., 1985, "Antibody–Directed Urokinase: A Specific Fibrinolytic Agent", Science 229:765–67.

Colwell et al, 1982, "IgA Hybridomas: A Method for Generation in High Numbers", J. Immunological Methods 54:259–66.

Ehrlich et al., 1983, "Monoclonal Antibodies to Alpha–Chain Regions of Human Fibrinogen That Participate in Polymer Formation", Biochemistry 22(18):4184–92.

Elms et al., 1983, "Measurement of Cross–Linked Fibrin Degradation Products—An Immunoassay Using Monoclonal Antibodies", Thromb. Haemostas. 50(2):591–94.

Francis et al., 1985, "Some studies with monoclonal antibody directed against human fibrinogen", Am. J. Hermat. 18:111–19.

Gaffney et al., 1985, "Unreliability of Current Serum Fibrin Degradation Product (FDP) Assay", Thromb. Haemostas. 53(3):301–2.

Hui et al., 1983, "Monoclonal Antibodies to a Synthetic Fibrin–like Peptide Bind to Human Fibrin but not Fibrinogen", Science 222:1129–32.

Hui et al., 1985, "Immunodetection of Human Fibrin Using Monoclonal Antibody–64C5 in an Extracorporeal Chicken Model", Thromb. Haemostas. 53(2):524–27.

Kanke et al., 1982, "Detection of Residual Coronary Thrombi After Reperfusion of Experimental Myocardial Infarction Using IN–111 Labeled Monoclonal Antifibrin Antibody", J. Nuclear Medicine 14(2):910; abstract No. 138.

Kennel et al., 1983, "Solid Phase Radioimmunoassay of Fragment D of Human Fibrinogen by Use of a Low Affinity Monoclonal Antibody", Clinical Chemistry 29(5):778–81.

Kennel, 1982, "Binding of Monoclonal Antibody to Protein Antigen in Fluid Phase or Bound to Solid Supports", J. Immunological Methods 55:1–12.

Koppert et al., 1985, "A Monoclonal Antibody, Specific for Human Fibrinogen, Fibrinopeptide A–Containing Fragments and Not Reacting with Free Fibrinopeptide A", Blood 66(3):503–507.

Kudryk et al., 1984, "Specificity of a Monoclonal Antibody for the NH$_2$—Terminal Region of Fibrin", Molecular Immunology 21(1):89–94.

(List continued on next page.)

*Primary Examiner*—Carol A. Spiegel
*Attorney, Agent, or Firm*—Pennie & Edmonds LLP

[57] ABSTRACT

An in vitro immunoassay to detect and quantitate soluble crosslinked and non-crosslinked DesAABB fibrin polymers in a sample from a subject. The assay can be used to support a diagnosis of, to evaluate, and to monitor, in a mammalian subject, a thrombotic event, including, but not limited to, myocardial infarction, pulmonary embolism, stroke and deep vein thrombosis.

22 Claims, 9 Drawing Sheets

OTHER PUBLICATIONS

Kudryk et al., 1983, "A Monoclonal Antibody With Ability to Distinguish Between NH$_2$—Terminal Fragments Derived From Fibrinogen And Fibrin", Mol. Immunology 20(11):1191–1200.

LaFrance et al., 1982, "IN 111 Antimyosin Monoclonal Antibody (AMAb) In Detecting Rejection of Heart Transplants", J. Nuclear Medicine 14(2):910; abstract No. 141.

McCabe et al., 1984, "A Diagnostic–Prognostic Test For Bladder Cancer Using A Monoclonal Antibody–based Enzyme–linked Immunoassay for Detection of Urinary Fibrin(ogen) Degradation Products", Cancer Res. 44:5886–93.

Müller–Berghaus et al., 1985, "Detection of Fibrin in Plasma by a Monoclonal Antibody Against the Amino–terminus of the Alpha–Chain of Fibrin", Scand. J.Clin. Lab. Invest. 45(178):145–151.

Needham et al., 1986, "Labeling Platelets with an Indium–labeled Monoclonal Antibody", J. Nuclear Medicine 27(6):975; abstract No. 404.

Pauwels et al., 1986, "Imaging of Thrombi with Tc–99m Labeled Fibrin–Specific Monoclonal Antibody, in a Rabbit Model", J. Nuclear Medicine 27(6):975; abstract No. 403.

Prowse, 1986, "Monoclonal Antibodies and the Haemostasis Laboratory: Current Position", Vox. Sang. 50:65–70.

Rosenbrough et al., 1986, "Purification of Fibrin–Specific Monoclonal Antibody From Ascites Fluid By Preparative Isoelectric Focusing", Immunology Letters 12:147–151.

Rylatt et al., 1983, "An Immunoassay for Human D–Dimer Using Monoclonal Antibodies", Thromb. Res. 31:767–78.

Scheefers–Borchel et al., 1985, "Discrimination Between Fibrin and Fibrinogen by Monoclonal Antibody Against a Synthetic Peptide", Proc. Natl. Acad. Sci. USA 82:7901–95.

Sobel et al., 1983, "Monoclonal Antibody to the Region of Fibronectin Involved in Cross–Linking to Human Fibrin", Biochemistry 22(18):4175–83.

Sola et al., 1983, "Isolation and Characterization of a Monoclonal Antibody Specific for Fibrinogen and Fibrin of Human Origin", Thromb. Res. 29:643–53.

Soria et al., 1983, "Monoclonal Antibodies that React Preferentially with Fibrinogen Degradation Products or with Cross–Linked Fibrin Split Products", Annals New York Academy of Sciences, pp. 665–66.

Underwood et al., 1985, "Hybrids From Normal, Germ Free, Nude and Neonatal Mice Produce Monoclonal Autoantibodies to Eight Different Intracellular Structures", Clin. Exp. Immunol 60:417–26.

Wilner et al., 1982, "Monoclonal Antibodies to Fibrinogen: Modulation of Determinants Expressed in Fibrinogen by gamma–Chain Crossing–Linking", Biochemistry 21(11):2687–92.

Yasuda et al., 1982, "Monoclonal Indium–111 Antimyosin Antibody Imaging Versus Right Ventricular Biopsy in the Diagnosis of Acute Myocarditis", J. Nuclear Medicine 14(2):910; abstract No. 139.

Bang and Chang, 1974, "Soluble Fibrin Complexes" in: Seminars in Thrombosis and Haemostasis, 1:91–128.

Brenner et al., 1989, "The Role of Soluble Cross–linked Fibrin in D–Dimer Immunoreactivity of Plasmic Digests", J. Lab. Clin. Med. 113:682–8.

Buller et al., 1991, "Deep Vein Thrombosis: New Non–Invasive Diagnostic Tests", Thromb. Haem. 66(1):133–37.

Dale et al., 1994, "Comparison of Three D–Dimer Assays for the Diagnosis of DVT: ELISA, Latex and an Immunofiltration Assay (NycoCard D–Dimer)", Thromb. Haemostas. 71(3):270–4.

Dinh et al., 1994, "Detection of Soluble Fibrin by Enzyme Immunoassay", Fibrinolysis (Conference Leuven, Belgium, Poster Presentation P–11: Assay Methodology, Abstract 350.

Eisenberg et al., 1985, "Fibrinopeptide A: A Marker of Acute Coronary Thrombosis", Circulation 71(5): 912–18.

Francis et al., 1989, "Increased Immunoreactivity of Plasma After Fibrinolytic Activation in an Anti–DD ELISA System", Circulation 79:666–73.

Francis et al., 1987, "Increased Plasma Concentrations of Cross–linked Fibrin Polymers in Acute Myocardial Infarction", Circulation 75(6):1170–77.

Gargan et al., 1988, "A Fibrin Specific Monoclonal Antibody Which Interferes With The Fibrinolytic Effect Of Tissue Plasminogen Activator", Thromb. Haemostas. 59(3):426–31.

Halvorsen et al., 1990, "Comparison of Methods for Detecting Soluble Fibrin in Plasma: An In Vitro Study", Thromb. Res. 57:489–97.

Haselager and Vreeken, 1981, "Clinical significance of 'circulating fibrin monomers'", J. Clin. Pathol. 34:468–72.

Hoegee–de Nobel et al., 1988, "A Monoclonal Antibody–Based Quantitative Enzyme Immunoassay For The Determination Of Plasma Fibrinogen Concentrations", Thromb. Haemostas. 60:415–18.

Hui et al, 1986, "Monoclonal Antibodies of Predetermined Specificity For Fibrin: A Rational Approach to Monoclonal Antibody Production", Hybridoma 5(3):215–222.

Hull et al., 1987, "Diagnosis of Deep Vein Thrombosis" In: Colman et al. (eds) Haemostasis and Thrombosis, J. P. Lippincott Co., Phila. pp. 1220–39.

Kudryk et al., 1991, "Fibrinogen–Fibrin: Preparation and Use of Monoclonal Antibodies As Diagnostics" in: Biotechnology, pp. 281–313.

Kudryk et al., 1990, "Monoclonal Antibodies as Probes For Fibrin(ogen) Proteolysis", in: *Monoclonal Antibodies in Immunoscintigraphy*, Chatal, J.F. (ed.) CRC Press, Boca Raton, FL, pp. 365–98.

Lill et al., 1993, "A New Immunoassay for Soluble Fibrin Enables a More Sensitive Detection of the Activation State of Blood Coagulation In Vivo", Blood Coag. and Fibrinol 4:97–102.

Niewenhuizen et al., 1992, "A Rapid Monoclonal Antibody–Based Enzyme Immunoassay (EIA) for the Quantitative Determination of Soluble Fibrin in Plasma", Thromb. Haemostas. 68(3):273–77.

Nieuwenhuizen, 1993, "Soluble Fibrin as a Molecular Marker for a Pre–Thrombotic State: A Mini–Review", Blood Coag. and Fibrinol. 4:93–96.

Okajima et al., 1989, "Characterization of the Fibrinolytic State by Measuring Stable Cross–linked Fibrin Degradation Products in Disseminated Intravascular Coagulation Associated with Acute Promyelocytic Leukemia", Acta Haematol. 81:15–18.

Selmayr and Muller–Berghaus, 1985, "Soluble Fibrin(ogen) Polymers", Thromb. and Haemostas. 54(4):804–07.

Vogel et al., 1990, "Predictive Value of Fibrin Monomers in Postoperative Deep Vein Thrombosis", Klin Wochenscher 68:1020–26.

Yudelman et al., 1978, "Plasma Fibrinopeptide A Levels In Symptomatic Venous Thromboembolism", Blood 51:1189–95.

Bos et al., "The Influence of Exogenous Antigenic Stimulation on the Specificity Repertoire of Background Immunoglobulin–Secreting Cells . . . ," Cell. Immunol. 112:371–80 (1988).

Francis et al., "Terminology for Macromolecular Plasmic Derivatives of Crosslinked Fibrin," Thromb. Haemost. pp. 110–111 (1987).

Matsueda et al., "Structural Basis for the Species Selectivity of a Fibrin—Specific Monoclonal Antibody," Biochem. (1986) 25: 1451–1455.

IMMUNOASSAY AND KIT FOR IN VITRO DETECTION OF SOLUBLE DESAABB FIBRIN POLYMERS

This is a division of application U.S. Ser. No. 086,423, filed Jul. 2, 1993, now U.S. Pat. No. 5,453,359, which is a continuation-in-part of application U.S. Ser. No. 081,914, filed Jun. 22, 1993, now abandoned, which is a continuation of application U.S. Ser. No. 835,800, filed Feb. 14, 1992, now U.S. Pat. No. 5,223,410 which is a continuation of U.S. Ser. No. 364,053, filed Jun. 8, 1989, now U.S. Pat. No. 5,120,834, which is a continuation-in-part of application U.S. Ser. No. 206,259, filed Jun. 13, 1988, now abandoned.

1. FIELD OF THE INVENTION

The subject invention relates a method for the production of monoclonal antibodies. The method utilizes an immunized germfree animal. The invention also provides a method for the use of such monoclonal antibodies, and polyclonal antibodies derived from an immunized germfree animal, for in vitro and in vivo clinical diagnostics and therapeutics. Also, the subject invention provides a fibrin-specific monoclonal antibody.

2. BACKGROUND OF THE INVENTION

Kohler and Milstein are generally credited with having devised the techniques that successfully resulted in the formation of the first monoclonal antibody-producing hybridomas (G. Kohler and C. Milstein, 1975, *Nature* 256, 495–497; 1976, *Eur. J., Immunol.* 6, 511–519). By fusing antibody-forming cells (spleen B-lymphocytes) with myeloma cells (malignant cells of bone marrow primary tumors) they created a hybrid cell line, arising from a single fused cell hybrid (called a hybridoma or clone). The hybridoma had inherited certain characteristics of both the lymphocytes and the myeloma cell lines. Like the lymphocytes, the hybridoma secreted a-single type of immunoglobulin; moreover, like the myeloma cells, the hybridoma had the potential for indefinite cell division. The combination of these two features offered distinct advantages over conventional antisera.

Antisera derived from vaccinated animals are variable mixtures of polyclonal antibodies which never can be reproduced identically. Monoclonal antibodies are highly specific immunoglobulins of a single type. The single type of immunoglobulins secreted by a hybridoma is specific to one and only one antigenic determinant, or epitope, on the antigen, a complex molecule having a multiplicity of antigenic determinants. For instance, if the antigen is a protein, an antigenic determinant may be one of the many peptide sequences (generally 6–7 amino acids in length; M. Z. Atassi, 1980, *Molec. Cell. Biochem.* 32, 21–43) within the entire protein molecule. Hence, monoclonal antibodies raised against a single antigen may be distinct from each other depending on the determinant that induced their formation; but for any given hybridoma, all of the antibodies it produces are identical. Furthermore, the hybridoma cell line is easily propagated in vitro or in vivo, and yields monoclonal antibodies in extremely high concentration.

A monoclonal antibody can be utilized as a probe to detect its antigen. Thus, monoclonal antibodies have been used in in vitro diagnostics, for example, radioimmunoassays and enzyme-linked immunoassays (ELISA), and in in vivo diagnostics, e.g. in vivo imaging with a radiolabeled monoclonal antibody. Also, a monoclonal antibody can be utilized as a vehicle for drug delivery to such antibodies' antigen.

However, before a monoclonal antibody can be utilized for such purpose, it is essential that the monoclonal antibody be capable of binding to the antigen of interest; i.e., the target antigen. This procedure is carried out by screening the hybridomas that are formed to determine which hybridomas, if any, produce a monoclonal antibody that is capable of binding to the target antigen. This screening procedure can be very tedious in that numerous, for example, perhaps several thousand, monoclonal antibodies may have to be screened before a hybridoma that produces an antibody that is capable of binding the target antigen is identified. Accordingly, there is the need for a method for the production of monoclonal antibodies that increases the likelihood that the hybridoma will produce an antibody to the target antigen.

3. SUMMARY OF THE INVENTION

The subject invention provides a method for the production of monoclonal antibodies to an antigen comprising:
(a) immunizing a germfree animal with said antigen to permit antibody-producing cells to produce antibodies to said antigen,
(b) removing at least a portion of said antibody-producing cells from said germfree animal,
(c) forming a hybridoma by fusing one of said antibody-producing cells with an immortalizing cell wherein said hybridoma is capable of producing a monoclonal antibody to said antigen,
(d) propagating said hybridoma, and
(e) harvesting the monoclonal antibodies produced by said hybridoma.

The subject invention also provides methods for utilizing a monoclonal antibody or a polyclonal antibody derived from a germfree animal. The subject invention also provides a fibrin-specific monoclonal antibody and methods for utilizing such a monoclonal antibody.

4. DETAILED DESCRIPTION OF THE INVENTION

4.1. THE GERMFREE ANIMAL

Figure 1A:
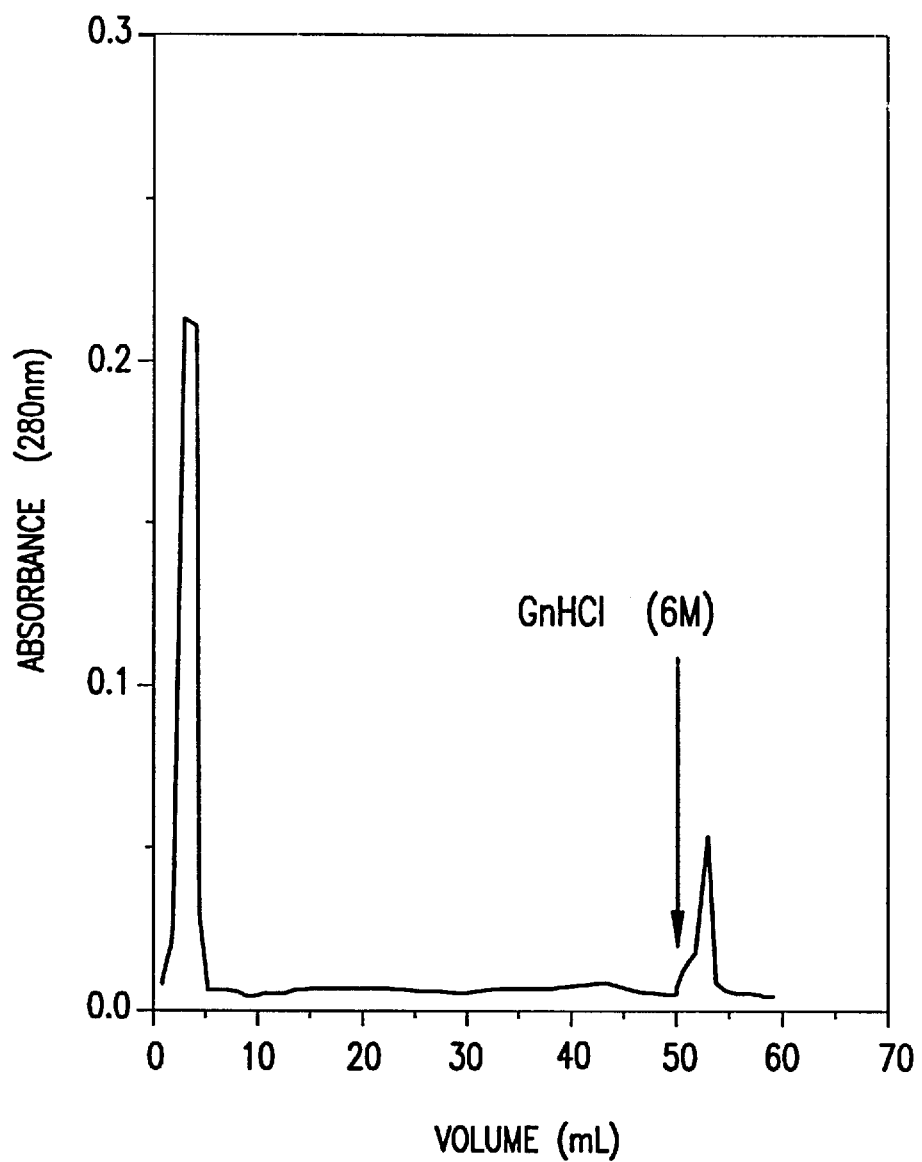
FIG. 1(A) Determination of immunoreactivity of MH1 with DesAABB fibrin monomer by affinity chromatography.

The subject invention relates to the use of a germfree animal for the production of monoclonal antibodies. Germfree animals were first developed in the latter part of the 19th century and have been utilized extensively since such time.

A germfree animal is a gnotobiote that is free from all demonstrable associated forms of life, including bacteria, viruses, fungi, protozoa, and other saprophytic or parasitic forms. A gnotobiote is an animal or strain derived by aseptic cesarean section or sterile hatching of eggs that is reared and continuously maintained with germfree techniques under isolator conditions and in which the composition of any associated fauna and flora, if present, is fully defined by accepted current methodology. (It should be noted that all mice carry a latent leukemogenic virus and, therefore, a mouse that would be germfree but for such leukemogenic virus shall be considered a germfree animal for the purpose of the subject invention.)

The essence of a germfree system is the provision of barriers against the entry of unwanted microbial invaders. In addition to the physical barriers of plastic, metal, rubber and glass which enclose the animals, the system requires the operational barriers of air filtration, food and water sterilization, and manipulation by gloves, which form an integral part of the barrier system. Also, the entry of supplies to the isolator should be performed under sterile conditions.

It is believed that any germfree animal can be utilized in the subject invention. The most common germfree animals are mouse, pig, rat, rabbit, guinea pig, goat, sheep, primate and poultry with a mouse being preferred, especially a BALB/c mouse.

4.2. PRODUCTION, CARE AND MAINTENANCE OF GERMFREE ANIMALS

There have been numerous publications concerning the production, care and maintenance of germfree animals. For example, Wostmann, B. S., Ed., Gnotobiotes: Standards and Guidelines for the Breeding, Care and Management of Laboratory Animals, National Research Council, National Academy of Sciences, Washington, D.C. 1970; Coates, M. E., et al., The Germfree Animal in Research, Academic Press, London, 1968; and Pleasants, J. R., Gnotobiotics, in Handbook of Laboratory Animal Science, Vol., 1, Melby, E. C., et al., Eds., CRC Press, Boca Raton, Fla., 117, (1974) the disclosures of which are incorporated herein by reference.

What follows is a summary derived from the article by Wostmann, B. S. ed., (1970) Gnotobiotes Standards and Guidelines for the Breeding, Care and Management of Laboratory Animals, National Research Council, National Academy of Sciences, Washington, D.C. describing the production, care and maintenance of germfree rats and mice. It should be noted that such production, care and maintenance is similar for other animals.

ROOM ENVIRONMENT

The facilities, equipment, and husbandry procedures shall be designed and operated so as to afford maximum environmental control and optimal comfort and welfare for the animals. The cages, feeders and waterers shall be so designed and fabricated as to afford maximum comfort for the animals, to make the food and water readily available, and to make cleaning and sterilization practicable and efficient.

A desirable floor plan for extensive germfree work should consist of:

1. a work area for assembling and sterilizing the isolators,
2. an area for maintaining the isolators with animals, and
3. a laboratory area for the routine monitoring of the gnotobiotic environment.

An office and diet-preparation area may be incorporated in the floor plan.

The room environment for maintaining gnotobiotic isolators should meet the standards established for housing conventional laboratory rodents. The structure should be insect-proof, and the walls and floor should be moisture-proof. Lighting should be uniform, with the same light-dark cycle throughout the year. Ventilation should rapidly remove any fumes caused by chemical sterilization, and the climate should be controlled as specified below.

Temperature. The generally accepted animal room temperature of 21°–27° C. (70°–80° F.) may need to be adjusted downward to keep the isolator temperature between 22° and 26° C. (72° and 78° F.).

Humidity. The relative humidity (RH) should be kept at the human comfort level of 40–60 percent. However, when room air is used to ventilate the isolator, 40–50 percent RH is recommended.

Ventilation. The room-air changes should be sufficient to remove rapidly any fumes generated during chemical sterilization. Ten to fifteen air changes per hour are recommended. Head masks with fresh-air ventilation should be available to protect personnel exposed to dangerous levels of chemical fumes.

GERMFREE EQUIPMENT (See Sacquet, E. 1968, Equipment design and management: General technique of maintaining germ-free animals, p. 1–22 In M. E. Coates. The germfree animal in research. Academic Press, London; Trexler, P. C. 1968. Equipment design and management: Transport of germ-free animals and current developments in equipment design, p. 23–35 In M. E. Coates [ed]. The germfree animal in research. Academic Press, London)

Complete exclusion of environmental microbes requires an absolute barrier. The successful operation of the isolator depends on the maintenance of that barrier at all times. There are two general types of isolators available, metal and plastic. Some metal units are built to withstand internal steam pressure of 20 psi (1,406 g/cm$^2$). (See Reyniers, J. A. 1959. Design and operation of apparatus for rearing germ-free animals. Ann. N.Y. Acad. Sci. 78:47; Miyakawa, M. 1959. The Miyakawa remote-control germfree rearing unit. Ann. N.Y. Acad. Sci. 78:37). Others are generally placed in a large autoclave for initial sterilization (See Gustafsson, B. E. 1959. Lightweight stainless steel systems for rearing germ-free animals. Ann. N.Y. Acad. Sci. 78:17.).

The flexible-film isolator (See Trexler, P. C., and L. I. Reynolds. 1957. Flexible film apparatus for the rearing and use of germfree animals. Appl. Microbiol. 5:406) is now the most widely used unit. It is usually made of flexible laminated vinyl, must be chemically sterilized, and is readily adapted to specific needs. Another type, made from a large tube of nylon, tied at each end, can be sterilized in an autoclave. (See Lev, M. 1962. An autoclavable plastic unit for rearing animals under germfree conditions. J. Appl. Bacteriol 25:30). Plexiglass isolators and disposable flexible-film units also have been developed. Many of these are light enough to be stacked two or three high on a rack, a feature that conserves floor space.

A special cylinder for sterilizing food and supplies is generally used with the heat-sensitive isolators. It should be designed with a large filtration area to facilitate air removal in a high-vacuum autoclave (See Trexler, P. C. 1963. An isolator system for control of contamination. Lab. Anim. Care. 13:572). Alternatively, the cylinder may be fitted with a drain tube vented to the atmosphere for removal of air and condensation during sterilization without the benefit of a vacuum. (See Jaworski, N. E., and C. E. Miller. 1963.

Refinement of the cylinder technique for supplying germfree isolators. Lab. Anim. Care. 13:591).

STERILIZATION

All equipment, food, bedding, water, and air used in the isolator must be absolutely sterile. The methods and conditions employed are determined by characteristics of the individual items.

Steam under pressure is the best-known method of sterilization. It is particularly suitable for porous items that are heat-stable. Every area that can conceivably harbor microbes must be brought into direct contact with steam. Exposure time is related to the temperature used. It is recommended that the least accessible portion of the load (the center of the packages) be exposed for a minimum period of 15 minutes at 121° C. (250° F.). Higher temperatures and shorter exposure periods may be used after careful testing to ensure sterility. Standard package size and density of diet, bedding, and other materials are of primary importance to assure that the steam penetration time will be constant and predictable.

Dry heat has been used for sterilization of the air supply for the isolator (See Miyakawa, M. 1959. The Miyakawa remote-control germfree rearing unit. Ann. N.Y. Acad. Sci. 78:37; Gustafsson, B. E. 1959. Lightweight stainless steel systems for rearing germ-free animals. Ann. N.Y. Acad. Sci. 78:17).

Peracetic acid ($CH_3COOOH$) is widely used on heat-sensitive, non-porous materials, especially the flexible-film units. This acid is used in a 2 percent solution with a wetting agent (detergent) (See Trexler, P. C., and L. I. Reynolds. 1957. Flexible film apparatus for the rearing and use of germfree animals. Appl. Microbiol. 5:406). Other chemicals can be used for special situations, e.g., hypochlorites, iodophors, or quarternary ammonium compounds in the liquid trap to introduce newborns obtained by hysterectomy, or $HgCl_2$ to introduce eggs under sterile conditions prior to hatching.

Ethylene oxide (ETO) may be used to sterilize nonwettable heat-sensitive items. Sterilization time is dependent on the temperature, humidity, pressure, and concentration of ETO. ETO may react chemically with bedding and dietary components to produce toxic or undesirable compounds. Because of its flammability and toxic hazards, routine use of ETO for sterilization should be restricted to the commercially available gas mixtures, which contain not more than 20 percent ETO.

Fiberglass filters are commonly used for sterilization of the air supply. They should function as absolute filters.

Membrane filtration of liquids can be used to avoid exposure to heat, provided these membranes are absolute filters, for example, a filter that excludes particles greater than 0.22 micrometers in diameter.

Irradiation by gamma rays or electron-beam sources may be used to sterilize diets or other special items. Dosages employed vary from 2.5 to $6 \times 10^6$ rads.

INTERNAL ENVIRONMENT

Temperature. The internal isolator temperature is a function of the room environment and should be maintained between 22° and 26° C. (72°–78° F.).

Humidity. The isolator is subject to condensation of moisture in cases of overloading, inadequate ventilation, or both. Air entering the isolator should be below 50 percent RH and preferably above 40 percent RH.

Air Supply. The isolator should have 12 to 20 air changes per hour and a positive pressure of 3–5 in. (8–13 cm) of water. Air may be supplied from a central source or from individual blowers for each unit. A turbine-type air compressor is recommended for a central air supply system because the oil piston type tends to atomize oil into the air-supply lines.

An air diffusion isolator (See Trexler, P. C. 1968. Equipment design and management: Transport of germ-free animals and current developments in equipment design, p. 23–35 In M. E. Coates [ed]. The germfree animal in research. Academic Press, London) is not subject to loss of ventilation in the event of power failure. However, this type has the disadvantage of fewer air changes per hour and lacks the protective positive pressure that could help prevent contamination should small breaks occur in the barrier.

Emergency Safeguards. Adequate provisions for the maintenance of air pressure within the isolator in the event of power failure or mechanical failure must be provided with not more than a few minutes' interruption in the air supply. Collapse of unsupported film isolators may eventually result in suffocation of the animals, but the more immediate danger is that the animals may be able to reach and damage film or gloves. This may be prevented temporarily by plugging air conduits with rubber stoppers. The operation of individual isolator air supplies requires only an emergency power supply. A central air system should have a second turbine compressor for standby air supply.

Graphic recording of the temperature and pressure is recommended. An audiovisual alarm system should be incorporated in a central air system to be actuated by a drop in line pressure in the event of either loss of power or mechanical failure. Similar alarm systems should indicate undesirable fluctuations in the temperature of the air supply. For individual isolator air systems, continuous graphic monitoring of the room environment is recommended.

CAGING AND INTERIOR EQUIPMENT

Equipment. A basic list of equipment for an isolator may include cages with secure lids, water bottles and food hoppers, protective cloth gloves for the rubber gloves, an extra door gasket or cap closing ring, long rubber-tipped forceps, hemostats, scissors, a towel, gauze sponges, a two-quart can for holding instruments, a covered four-quart diet can, spoon, culture tubes, paper bags, and moisture-resistant bags for dirty bedding.

Cages should be fabricated of a smooth corrosion-resistant material. They should be impervious to liquids and easily sterilized. Materials considered acceptable include plastics, stainless steel, and glass. Galvanized metal becomes corroded and is not recommended because trace-metal contamination may influence experimental results.

Cage dimensions are usually limited by the size of the entry port. The minimum area for a female mouse-and litter is 50 in.$^2$ (970 cm$^2$). In many circumstances more space per animal may be needed.

Table 1 lists the recommended floor space per animal for mice and rats according to weight groupings.

TABLE 1

Amount of Floor Space Recommended per Animal for Caged Mice and Rats

| Category Number | Weight(g) | Space per Animal in.$^2$ (cm$^2$) | Maximum Population Per Cage |
|---|---|---|---|
| | | MICE | |
| 1 | up to 10 | 6 ( 40) | 40 |
| 2 | 10–15 | 8 ( 50) | 30 |
| 3 | 15–25 | 12 ( 75) | 20 |
| 4 | over 25 | 15 ( 95) | 16 |

TABLE 1-continued

Amount of Floor Space Recommended per Animal for Caged Mice and Rats

| Category Number | Weight(g) | Space per Animal in.² (cm²) | Maximum Population Per Cage |
|---|---|---|---|
| RATS | | | |
| 1 | up to 50 | 15 ( 95) | 50 |
| 2 | 50–100 | 17 (110) | 50 |
| 3 | 100–150 | 19 (125) | 40 |
| 4 | 150–200 | 23 (150) | 40 |
| 5 | 200–300 | 29 (185) | 30 |
| 6 | over 300 | 40 (260) | 25 |

MISCELLANEOUS RECOMMENDATIONS

Freon tests for minute leaks are recommended to ensure the integrity of the barrier system.

Each unit should be equipped with its own operation log to maintain a chronological record of every procedure involving the unit from the time it is assembled and sterilized. Such records are conveniently kept in metal hospital-chart holders identified by the isolator number. They should also contain notes for routine maintenance, e.g., glove replacement. Breeding-performance records may be kept in the same chart holder.

Due to the limited space available inside the isolators, paper and folding containers are recommended for diets and bedding, and for the transport of animals between isolators linked by a sterile passage.

No ether should be used inside an isolator because it may explode when static sparks occur. Fluothane (bromochlorotrifluoroethane) is recommended as a volatile, nonflammable anesthetic.

DIETS, BEDDING AND WATER
GENERAL RECOMMENDATIONS

The complete formula for commercially produced diets should be provided, listing all the ingredients and their concentrations, including preservatives, antioxidants, and other additions. The date of production should be clearly indicated. The manufacturer should guarantee that the diet is:

1. Within the normal acceptable limits of naturally occurring hormone activity.
2. Free of additives containing drugs, hormones, antibiotics, or any other substance that may create abnormal physiological conditions or interfere with investigative procedures.
3. Free of salmonella on the basis of statistically selected samples.
4. Free of rodent and vermin contamination.
5. Free of all unrendered meat scraps or fish meal that may contain pathogens.

FORTIFICATION OF DIETS

Diets of germfree animals must contain more than normal requirements of certain nutrients to compensate for the heat-sterilization loss of vitamins (especially certain B vitamins and vitamins A and D) and of the nutritive value of protein (reduction in available lysine, methionine, arginine and tryptophan). They must also provide required nutrients, which in conventional animals would be available through microbial synthesis in the gastrointestinal tract (See Reddy, B. S., B. S. Wostmann, and J. R. Pleasants. 1968. Nutritionally adequate diets for germ-free animals, p. 87–111 In M. E. Coates [ed]. The germ-free animal in research. Academic Press, London). An example of such a diet is L-485, an inexpensive diet that has been extensively tested (See Kellogg, T. F., and B. S. Wostmann. 1969. Rat and mouse stock diet L-485. Lab. Anim. Care.) and can be commercially produced (see Table 2). Supplementation with specific amino acids rather than increased total protein content should be considered as a means to compensate for loss in protein quality. Increasing the total protein content of the diet will result in a greater consumption and excretion of water, causing humid conditions and thereby limiting the number of animals that can be housed in an isolator of a given size.

TABLE 2

Composition of Diet L-485 for Rats and Mice

| Ingredient | Amount per kg |
|---|---|
| DIET | |
| Ground yellow corn (maize) | 590 g |
| Soybean oil meal (crude protein 50 percent) | 300 |
| Alfalfa meal (dehydrated; 7 percent protein) | 35 |
| Corn oil (once refined) | 30 |
| NaCl | 10 |
| $CaHPO_4 \; 2H_2O$ | 10 |
| $CaCO_3$ | 5 |
| Lysine (feed grade) | 5 |
| Methionine (feed grade) | 5 |
| B.H.T. (butylated hydroxytoluene) | 0.125 |
| Trace mineral mix | 0.25 |
| VITAMIN MIX | |
| A | 26,000 IU |
| $D_3$ | 1,000 IU |
| E ($\alpha$ tocopherol acetate) | 225 mg |
| $K_3$ (menadione) | 90 |
| Riboflavin | 30 |
| Pantothenic acid | 285 |
| Niacin | 65 |
| Choline chloride | 2,000 |
| $B_{12}$ (0.1 percent trituration in mannitol) | 2 |
| Thiamine HCl | 65 |
| Pyridoxine HCl | 20 |
| Folic acid | 10 |
| Para-aminobenzoic acid | 50 |
| TRACE MINERAL MIX (commercial | |
| Mn as manganous oxide | 65 mg |
| Fe as ferrous carbonate | 20 |
| Cu as copper oxides | 2 |
| Zn as zinc oxide | 15 |
| I as calcium iodate | 1.5 |
| Co as cobalt carbonate | 0.6 |

Steam sterilization (See Reddy, B. S., B. S. Wostmann, and J. R. Pleasants. 1968 Nutritionally adequate diets for germ-free animals, p. 87–111 In M. E. Coates The germ-free animal in research. Academic Press, London)

Actual procedures will depend on the equipment available. Three factors are of general importance:

1. A pre-sterilization vacuum, whenever possible, of at least 20 in. Hg will assist steam penetration of the diet in a clave or cylinder vented to the atmosphere. A vacuum of 28 in. Hg or more is recommended when the supply cylinder is not vented to the atmosphere.
2. Use of the shortest sterilization phase that will ensure total sterility, with an added safety margin dictated by equipment and skill. Temperatures measured at the inner core of the diet should reach at least 121° C. (250° F.). At that temperature the actual sterilization phase should last a minimum of 15 minutes. With higher sterilization temperatures, sterilization times will be relatively shorter.
3. A post-sterilization vacuum will speed the reduction of temperature of the diet. This will avoid unnecessary heat destruction of nutrients. However, the design and performance of the apparatus must be adequate to avoid leaks during this stage of the operation.

In steam sterilization of diets, the goal is to avoid both incomplete sterilization and unnecessary nutritional damage caused by excessively prolonged heating. Although some nutrient loss is unavoidable, quite acceptable results may be obtained by manipulation of:

(a) Technical procedures such as temperature, time pre-sterilization and post-sterilization vacuum, and pellet size.

(b) The water content of the diet. An increase in water content leads to better recovery of B vitamins after sterilization (See Zimmerman, D. R., and B. S. Wostmann. 1963. Vitamin stability in diets sterilized for germfree animals. J. Nutr. 79:318). For solid diets, a water content up to 25 percent, or as high as proves to be compatible with the storage quality of the diet, is recommended. A change in water content of the diet should be followed by a new test of the rate at which the diet reaches sterilizing temperature.

RADIATION STERILIZATION (See Reddy, B. S., B. S. Wostmann, and J. R. Pleasants. 1968. Nutritionally adequate diets for germ-free animals, p. 87–111 In M. E. Coates [ed]. The germ-free animal in research. Academic Press, London; Ley, F. J., J. Bleby, M. E. Coates, and J. S. Paterson. 1969. Sterilization of laboratory animal diets using gamma radiation. Lab. Anim. 3:221)

Techniques and dosimetry will depend on equipment and type of radiation. Although, in general, radiation sterilization is considered to result in less destruction of nutrients, it is at present recommended that diets be sterilized with steam.

TEST FOR STERILITY

To monitor sterility achieved with any specific sterilization procedure, the use of *Bacillus stearothermophilus* spore strips is recommended. The strips should be embedded in the core of the diet. Also, the isolator and its animals should be periodically microbiologically monitored. Such monitoring is necessary to test for accidental contaminations resulting from breaks in the isolator barriers or from inadequate sterilization of the isolator or its contents. This can be accomplished as described in Wostmann, B. S., Ed., Gnotobiotes: Standards and Guidelines for the Breeding, Care and Management of Laboratory Animals, National Research Council, National Academy of Sciences, Washington, D.C., 1970, pp. 28–39.

ESTIMATION OF NUTRIENT LOSS DURING STERILIZATION

As a useful check on the loss of vital nutrients, determination of acid-extractable thiamine as an indicator of the recovery of thiamine added to the diet is recommended (See Wostmann, B. S. and P. L. Knight. 1960. The effect of methyl alcohol on the conversion of thiamine to thiochrome. Experientia 16:500). A recovery of less than 25 percent indicates severe impairment of general nutritional quality of the diet. With adequate equipment and care, recoveries of 50 percent or more should be achieved.

STORAGE OF SOLID DIET

Because of the generally high cost of germfree experimentation, extra care should be taken never to use diet that has decreased significantly in nutritional value. It is recommended that (a) nonsterilized diet always be stored under refrigeration, and never for longer than one month, and that (b) storage time of sterilized diet inside the isolator should be one week or less and must never exceed ten days.

BEDDING

Bedding should be changed at least once a week. It is recommended that bedding material be easy to sterilize and not readily eaten by the animals. It should not yield toxic compounds as a result of the sterilization procedure. Dust-free white pine chips (sawdust) and shavings are recommended. Basswood and poplar shavings or crushed corn cobs are acceptable. Diatomaceous products, cedar, resinous woods, and hardwoods are not recommended. Ethylene oxide sterilization should not be used until the question of possible formation of harmful compounds has been clarified.

WATER

Drinking water must be sterilized. It may be autoclaved in square pack flasks, Mason jars, or tanks attached to the unit. A small air space should be left inside each container.

PRINCIPLES OF CESAREAN DERIVATION OF GNOTOBIOTES

The success of any cesarean operation is keyed in part to having the pregnancy advance to full term. This is particularly true of animals with short gestation periods, where the fetus may gain 20 percent of its weight in the final 24 hours before parturition. Timed matings are reasonably successful, but with animals yielding large litters (rats and mice) it may be helpful to wait for the female to deliver the first offspring before proceeding with the operation. In guinea pigs, the most satisfactory method is to select females for surgery by measuring the spread of the pubic bones (See Philips, B. P., P. A. Wolfe, and H. A. Gordon. 1959. Studies on rearing the guinea pig germfree. Ann. N.Y. Acad. Sci. 78:183).

The cesarean-derived young must be delivered into a germfree environment before they take their first breath of air. They may be taken directly from the mother by hysterotomy, through an incised sterile barrier membrane into a sterile isolator, or by hysterectomy, through a germicidal trap into a sterile isolator. The usual surgical preparation of the female prior to the cesarean operation includes removal of abdominal hair and cleaning and disinfection of the operative site. Anesthesia is accomplished preferentially by dislocation of the cervical vertebrae in rats and mice, although an abdominal midline local anesthetic or general anesthesia may also be used without incurring serious levels of fetal depression and mortality. With guinea pigs, surgery is generally performed after prior sedation and under local anesthesia.

Delivery of the young by hysterotomy through a barrier membrane requires special isolator equipment. The Reyniers stainless-steel surgical unit (See Reyniers, J. A. 1965. Germfree life methodology (gnotobiotics) and experimental nutrition. p. 458–466 In Proc. 3rd Internat. Congr. Biochem., Bruxelles) has a built-in horizontal metal divider that separates the upper and lower compartments of the unit. The divider contains a circular port covered with a mylar plastic film to maintain the integrity of the upper compartment. The female, prepared for surgery, is placed in the lower compartment with the abdomen pressed against the mylar. All surgical instruments are in the upper compartment, and the surgery is performed in this sterile area. An incision is made through the plastic and skin with an electrocautery or scalpel. The self-sterilizing electrocautery blade is preferred for skin incision. The edges of the skin and mylar are clamped together and reflected. A sterile drape is placed over the abdomen to cover the cut edges of the skin, and warm disinfectant (benzalkonium chloride 1:1,000) is applied to the exposed fascia before opening the abdominal cavity. Extreme caution must be exercised to avoid cutting into the bowel. The insertion of a pair of forceps or hemostats between the peritoneal wall and the viscera may be helpful. The uterus is then opened and the young removed. The fetal membranes are removed, and the umbilical cord is clamped and cut. The young are gently dried and massaged to stimulate respiration. They are then transferred to a rearing unit to be foster-nursed or hand-fed. Another sheet of mylar may be secured over the surgical port and the procedure repeated with as many as 5 or 6 females without serious risk of contamination. Cesarean delivery may also be accomplished using a plastic isolator or glove bag as a surgical unit. The exterior surface of the isolator floor is presterilized and brought into contact with the animal's abdomen, thus serving the same purpose as the mylar sheet described above. Following the operation the slit in the plastic barrier can be closed with sterile tape and the surgical procedure repeated on additional gravid females.

Delivery of the young by hysterotomy is more common when plastic isolators are used (See Foster, H. 1959. A procedure for obtaining nucleus stock for a pathogen-free animal colony. Lab. Anim. Care 9:135). The uterus is aseptically exposed and clamped just anterior to the cervix. The excised uterus is transferred into the germfree unit through a liquid germicidal trap. Once inside the isolator, the young are delivered as rapidly as possible to prevent aspiration of fetal fluids. Normally they are dried and breathing well before the umbilical cord is clamped and cut. The infants are then given to the foster mother or hand reared.

Hysterotomy may be used successfully for mice, rats, and swine. In guinea pigs, however, hysterotomy is preferred, since a high mortality occurs if as much as two minutes elapses between the severance from the maternal blood supply and delivery inside the isolator.

BREEDING SYSTEMS IN GNOTOBIOTIC COLONIES INBRED STRAINS

The usual brother X sister mating system employed in conventional breeding colonies can also be used in gnotobiotic colonies.

NONINBRED STOCKS

True random breeding includes some matings of siblings and of first cousins. Although such matings are normally avoided in noninbred breeding colonies, the resulting mating system does not decrease the rate of inbreeding to the maximum extent possible. Any system of minimal inbreeding can be used. (See Falconer, D. C. 1967. Genetic aspects of breeding methods. p. 72–96 In The UFAW handbook on the care and management of laboratory animals, 3rd ed. E and S Livingstone, LTd., London; National Research Council, Institute for Laboratory Animal Resources. 1969. A guide to genetic standards for laboratory animals. National Academy of Sciences, Washinton, D.C.).

Comparable Conventional and Gnotobiotic Colonies

If it is desired to maintain both conventional and gnotobiotic colonies for comparative purposes, their similar genetic constitutions may be maintained by introducing cesarean-derived litters from the effective breeding population of the conventional colony into the gnotobiotic colony. This appears to be the method of choice for those producers who place most emphasis on the production of nongnotobiotic rats and mice but has the disadvantage of preventing the establishment of a microbiological pedigree that would simplify microbiological monitoring. Ideally, this could be done by using litters from specific matings as breeding stock for the conventional colony and using the next litter from each of these matings as breeding stock for the gnotobiotic colony. If this procedure is followed every second or third generation, the genetic constitutions of both colonies should remain very similar, provided, of course, that the same mating system is used in each colony.

Alternatively, litters from the effective breeding population of the gnotobiotic colony may be used to establish or replenish the conventional colony. The genetic consequences will be identical, provided the same procedures are followed.

RECORD-KEEPING (See Wolff, G. L. 1967. Practical mating systems and record-keeping in a breeding colony. p. 97–113 In the UFAW handbook on the care and management of laboratory animals, 3rd ed. E. and S Livingstone, Ltd., London).

Proper records should be kept for the animals and for the maintenance of the isolator. The animals' records should determine the efficiency of the operation and the biological performance of the animals. The isolator records should maintain a chronology of events related to the isolator to assist in locating a breach of the barrier if contamination occurs.

4.3. THE ANTIGEN-FREE ANIMAL

In a preferred embodiment of the subject invention, it is preferred that the germfree animal be bred on a chemically defined (CD), low molecular weight, water-soluble, ultrafiltered diet. It is believed that such a diet permits one to obtain complete control of nutrient and antigen intake by the animal. Such a diet is generally made up entirely of ingredients that are capable of chemical definition, e.g., amino acids, simple sugars, lipids, vitamins and minerals. For the purpose of the subject invention a chemically defined diet comprises amino acids, simple sugars, lipids, vitamins and minerals and no other component having a molecular weight greater than about 10,000 daltons. Thus, all of the components of a CD diet are of low molecular weight and are naturally circulating nutrients in animals and, therefore, it is believed that such components will not stimulate an immune response. The recent literature refers to a germfree animal that has been bred on a CD diet as an "antigen-free animal".

Also, it is preferred to utilize a filter paper bedding, otherwise the germfree animal may eat the bedding, which results in an immune response. It is believed that the eating of a filter paper bedding does not result in an immune response.

The particular CD diet for a given species would use such components in proportions and quantities so as to fulfill known nutritional requirements for such species. The composition and preparation of a preferred CD diet for germfree mice is as follows:

| Composition and preparation of chemically defined diet L489E14Se | |
|---|---|
| Ingredient | Amount (g/100 g) |
| To 192 ml Milli-Q water at 70° C. the following are added: | |
| Leucine | 1.9 |
| Phenylalanine | 0.74 |
| Isoleucine | 1.08 |
| Methionine | 1.06 |
| Tryptophan | 0.37 |
| Valine | 1.23 |
| Asparagine | 0.91 |
| Arginine HCl | 0.81 |
| Threonine | 0.74 |
| Lysine HCl | 1.77 |
| Histidine HCl.H$_2$O | 0.74 |
| The solution is cooled to 45° C. and the following added: | |
| Glycine | 0.59 |

-continued

| | |
|---|---|
| Proline | 1.48 |
| Serine | 1.33 |
| Alanine | 0.59 |
| Sodium glutamate | 3.40 |
| L-tyrosine ethyl ester HCl | 0.62 |
| Ferrous gluconate | 0.05 |
| Salts 35D[1] | 0.105 |
| Sodium Selenite[2] | 0.074 |
| Solution cooled to 5° C. and the following added: | |
| Calcium glycerophosphate | 5.22 |
| Magnesium glycerophosphate | 1.43 |
| Calcium chloride 2H$_2$O | 0.185 |
| Sodium chloride - Potassium Iodide (KI) mix (containing 680 μg Ki) | 0.086 |
| Vitamin B mix 111E5[3] | 0.09 |
| Vitamin B12[4] | 1.20 mg |
| Choline chloride | 0.31 |
| Potassium acetate | 1.85 |
| To 108 ml Milli-Q water at 70° C. | |
| D-Dextrose, anhydrous was added | 71.28 |

Solutions cooled to 5° C. and combined both for ultrafiltration.
[1]Composition of salts 35D mixture given in Table 5
[2]Added in addition to sodium selenite in Salts 35D
[3]Composition of vitamin B mix111E5 as stated in Table 6
[4]Added in addition to vitamin B-12 in vitamin B mix 111E5 (see EXAMPLE hereinbelow)
Such composition is fed to mice or rats ad libitum.

Composition of lipid supplement LADEK 69E6

| Ingredient | Amount per daily adult dose* (0.385 ml) |
|---|---|
| Purified soy triglycerides[1] | 0.33 g |
| Retinyl palmitate | 6.45 μg (11.7 I.U.) |
| Cholecalciferol | 0.0288 μg (1.15 I.U.) |
| 2ambo-alpha-tocopherol | 3.3 mg |
| 2ambo-alpha-tocopherol acetate | 6.6 mg |
| Phylloquinone | 72 μg |

*Lactating mice receive twice the normal adult dose.
[1]consisting of:
12% palmitate
1.5% stearate
24% oleate
55% linoleate
8% linolenate For a detailed description of CD diets see Pleasants, J. R., et al., *J. Nutr.*, 116, 1949–1964 (1986), Pleasants, J., et al., *Germfree Research: Microflora Control and Its Application to the Biomedical Sciences*, B. S. Wostmann, Ed., p. 87, Liss, New York (1985); Wostmann, B. S., et al., *J. Nutr.*, 112, 552 (1982); and Pleasants, J. R., et al., *J. Nutr.*, 100, 498 (1970), the disclosures of which are incorporated herein by reference.

4.4 PRODUCTION OF MONOCLONAL ANTIBODY

The germfree animal is then utilized for the production of monoclonal antibodies. The germfree system can be utilized to produce a monoclonal antibody to any antigen that the animal in a nongermfree state could produce. An examplary list of antigens appears in U.S. Pat. 3,935,074. However, it is believed that the germfree animal provides a much enhanced immune response to the antigen. Thus, one can increase the likelihood of locating a B-lymphocyte that produces an antibody that is capable of binding to a specific epitope of the antigen. This is a major advantage of the subject invention. In addition, it is believed that the germfree system is particularly useful for generating a highly specific antibody for those antigens with numerous epitopes.

The germfree animal can be immunized by standard techniques. However, it is preferred that the germfree animal be immunized at least three times with at least about three weeks between each immunization, followed by a prefusion booster. It is believed that this increased level of immunization may be necessary because it has been observed that after two immunizations, which is customary, there are still mostly IgM secreting B-lymphocytes rather than the preferred IgG secreting B-lymphocytes.

4.5. SOMATIC CELLS

Somatic cells of the germfree animal having the potential for producing antibody and, in particular B lymphocytes, are suitable for fusion with a B-cell myeloma line. Those antibody-producing cells that are in the dividing plasmablast stage fuse preferentially. Somatic cells can be derived from the lymph nodes, spleens and peripheral blood of primed germfree animals, and the lymphatic cells of choice depend to a large extent on their empirical usefulness in the particular fusion system. However, somatic cells derived from the spleen are generally preferred. Once primed or hyperimmunized, germfree animals can be used as a source of antibody-producing lymphocytes. Mouse lymphocytes give a higher percentage of stable fusions with the mouse myeloma lines described hereinbelow. However, the use of antibody-producing cells from other germfree animals is also possible. The choice of a particular germfree animal depends on the choice of antigen, for it is essential that the germfree animal have a B-lymphocyte in its repertoire of B-lymphocytes that can produce an antibody to such antigen.

4.6. IMMORTALIZING CELLS

Specialized myeloma cell lines have been developed from lymphocyte tumors for use in hybridoma-producing fusion procedures (G. Kohler and C. Milstein, 1976, Eur. J. Immunol. 6:511–519; M. Schulman et al., 1978, Nature 276:269–270). The cell lines have been developed for at least three reasons. The first reason is to facilitate the selection of fused myeloma cells. Usually, this is accomplished by using myelomas with enzyme deficiencies that render them incapable of growing in certain selective media that support the growth of hybridomas. The second reason arises from the inherent ability of lymphocyte tumor cells to produce their own antibodies. The purpose of using monoclonal techniques is to obtain immortal fused hybrid cell lines that produce the desired single specific antibody genetically directed by the somatic cell component of the hybridoma. To eliminate the production of tumor cell antibodies by the hybridomas, myeloma cell lines incapable of producing light or heavy immunoglobulin chains or those deficient in antibody secretion mechanisms are used. A third reason for selection of these cell lines is their suitability and efficiency for fusion.

Several myeloma cell lines can be used for the production of fused cell hybrids, including NS-1, X63-Ag8, NIS-Ag4/1, MPC11-45.6TG1.7, X63-Ag8.653, Sp2/O-Agf14, FO, and S194/5XXO.Bu.1., all derived from mice, and 210-.RCY3.Agl.2.3 derived from rats. (G. J. Hammerling, U. Hammerling and J. F. Kearnly, eds., 1981, Monoclonal antibodies and hybridomas In J. L. Turk, eds. Research Monographs in Immunology, Vol. 3, Elsevier/North Holland Biomedical Press, New York).

4.7. FUSION

Methods for generating hybrids of antibody-producing spleen or lymph node cells and immortalizing cells generally comprise mixing somatic cells with immortalizing cells in a proportion which can vary from about 20:1 to about 1:1 in the presence of an agent or agents (chemical, viral or electrical) that promote the fusion of cell membranes. It is often preferred that the same species of animal serve as the source of the somatic and immortalizing cells used in the fusion procedure. Fusion methods have been described by Kohler and Milstein (1975, Nature 256:495–497; 1976, Eur. J. Immunol. 6:511–519), by Gefter et al. (1977, Somatic Cell Genet. 3:231–236) and by Kozbor et al., 1983, Immunology Today, 4, 72. The fusion-promoting agents used by those investigators were Sendai virus and polyethylene glycol (PEG), respectively.

One can also utilize the recently developed EBV-transformation technique (Cole et al., 1985, Monoclonal Antibodies and Cancer Therapy, Alan R. Liss, Inc., pp. 77–96).

4.8. ISOLATION OF CLONES AND ANTIBODY DETECTION

Fusion procedures usually produce viable hybrids at very low frequency, about $1 \times 10^{-6}$ to $1 \times 10^{-8}$. Because of the low frequency of obtaining viable hybrids, it is essential to have a means to select fused cell hybrids from the remaining unfused cells, particularly the unfused myeloma cells. A means of detecting the desired antibody-producing hybridomas among the other resulting fused cell hybrids is also necessary.

Generally, the fused cells are cultured in selective media, for instance HAT medium, which contains hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells can synthesize purine using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT media are hybrids formed from myeloma and spleen cells.

To facilitate screening of antibody secreted by the hybrids and to prevent individual hybrids from overgrowing others, the mixture of fused myeloma and B-lymphocytes is diluted in HAT medium and cultured in multiple wells of microtiter plates. In two to three weeks, when hybrid clones become visible microscopically, the supernatant fluid of the individual wells containing hybrid clones is assayed for specific antibody production.

The assay must be sensitive, simple and rapid. Assay techniques include radioimmunoassays, enzyme immunoassays, cytotoxicity assays, and plaque assays.

4.9. CELL PROPAGATION AND ANTIBODY PRODUCTION

Once the desired fused cell hybrids have been selected and cloned into individual antibody-producing cell lines, each cell line can be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines can be propagated in vitro in laboratory culture vessels. The culture medium, containing high concentrations of a single specific monoclonal antibody, can be harvested by decantation, filtration or centrifugation.

4.10. USE OF THE MONOCLONAL ANTIBODY

The monoclonal antibodies made by the method of the subject invention can be utilized in any technique known or to be developed in the future that utilizes a monoclonal antibody.

A major use of monoclonal antibodies is in an immunoassay, which is the measurement of the antigen-antibody interaction. Such assays are generally heterogeneous or homogeneous. In a homogeneous immunoassay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, fluorescent dyes, enzymes, bacteriophages, coenzymes, and so forth. The major advantage of a homogeneous immunoassay is that the specific antibody need not be separated from the labeled analyte.

In a heterogeneous immunoassay, the reagents are usually the specimen, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescers, enzymes, and so forth. Exemplary of heterogeneous immunoassays are the radioimmunossay, immunofluoroescence methods, enzyme-linked immunoassays, and the like.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817, 837; 3,850,578; 3,853,987; 3,867,517; 3,901,654; 3,935, 074; 3,984,533; 3,996,345; and 4,098,876, which listing is not intended to be exhaustive.

Another major use of monoclonal antibodies is in-vivo imaging and therapeutics. The monoclonal antibodies can be labelled with radioactive compounds, for instance, radioactive iodine, and administered to a patient intravenously. The antibody can also be labelled with a magnetic probe. NMR can then be utilized to pinpoint the antigen. After localization of the antibodies at the antigen, the antigen can be detected by emission tomographical and radionuclear scanning techniques, thereby pinpointing the location of the antigen.

By way of illustration, the purified monoclonal antibody is suspended in an appropriate carrier, e.g., saline, with or without human albumin, at an appropriate dosage and is administered intravenously, e.g., by continuous intravenous infusion over several hours, as in Miller et al. In Hybridomas in Cancer Diagnosis and Therapy (1982), incorporated herein by reference.

The monoclonal antibodies of subject invention can be used therapeutically. Antibodies with the proper biological properties are useful directly as therapeutic agents. Alternatively, the antibodies can be bound to a toxin to form an immunotoxin or to a radioactive material or drug to form a radiopharmaceutical or pharmaceutical. Methods for producing immunotoxins and radiopharmaceuticals of antibodies are well-known (see, for example, *Cancer Treatment Reports* (1984) 68:317–328).

It also is believed that polyclonal antibodies derived from a germfree animal also can be utilized in immunoassays and provide an improved result as compared to polyclonal antibodies derived from a conventional animal. Polyclonal antibodies derived from a germfree animal can be made by utilizing a germfree animal, as described hereinabove, and immunization techniques, as described hereinabove, followed by separating the polyclonal antibodies from the animal by conventional techniques, e.g. by separating the serum from the animal.

5. A FIBRIN-SPECIFIC MONOCLONAL ANTIBODY

5.1. BACKGROUND

The hemostatic mechanism is a complex physiological response mechanism involved in repairing damage to a ruptured blood vessel. Hemostasis is achieved through the co-operative interactions among the wall of the damaged blood vessel, the platelets and the coagulative system. The role of the coagulation system is to provide an extensive fibrin network to stabilize and anchor the platelet plug which has been assembled on the subendothelial structure of the damaged vessel. The formation of the insoluble fibrin matrix from circulating fibrinogen is the result of a complex sequence of reactions culminating in the explosive production of thrombin at the required site. Coagulation is an amplification process involving a chain of enzymatic reactions in which proenzymes (clotting factors) are activated sequentially to active enzymes. There are a number of physiological mechanisms controlling the fibrin polymerization process involved in thrombus formation. These include the thrombin inhibitor antithrombin III (ATIII), protein C, prostacyclin and various components of the fibrinolytic system such as tissue plasminogen activator (t-PA) and its fast acting inhibitor (PAI).

The homeostasis hypothesis proposed by Astrup in 1956 Astrup, T., *Blood* 11, 781–806 (1956) states than an equilibrium exists between fibrin formation (coagulation) and fibrin dissolution (fibrinolysis). In the normal or healthy state these functions are evenly balanced. However, when the hemostatic process is impaired, coagulation and fibrinolysis are pathologically expressed as thrombosis and hemorrhage, respectively. The clinical manifestations of pathological thrombosis or thrombotic disease are extremely diverse and include disseminated intravascular coagulation (DIC), deep vein thrombosis (DVT), arterial and venous thrombosis. Thromboembolism and thrombotic complications of other vascular disease (e.g. atherosclerosis) can result in occlusion of major arteries leading to organ ischemia and the attendant life-threatening conditions such as cerebrovascular accident (stroke), myocardial infarction, etc.

The fibrinolytic process involves the conversion of an inactive zymogen, plasminogen, to the proteolytic enzyme, plasmin, through the action of agents known as plasminogen activators. The molecular mechanism of physiological fibrinolysis is not fully understood, but it is known that during fibrin formation plasminogen binds to fibrin where it can be activated by plasminogen activators, e.g. t-PA. In this manner plasmin generation proceeds within the thrombus where it is protected from inactivation by the main physiological inhibitor of plasmin, alpha$_2$-antiplasmin.

Upon exposure to plasmin, fibrinogen and fibrin are broken down to their degradation products. Fibrinogen breaks down into fragments X and Y, and upon further exposure to plasmin, fragments D and E. Fibrin breaks down to fragments X, Y, D and E from non-crosslinked fibrin and crosslinked D-dimer, D-D/E complex, Y dimer, Y-D-dimer and X oligomer from crosslinked fibrin.

Assays for markers of thrombotic disorders have been conducted until quite recently using polyclonal antibodies in both radioimmunoassays and latex agglutination type assays. These assays have been demonstrated to be extremely unreliable by Gaffney (Gaffney, P. J., *Ann. N.Y. Acad. Sci.,* 408, 407–423 (1983). More specific and sensitive immunoassays (such as ELISAs) using monoclonal antibodies are becoming common practice in clinical laboratories. The limiting factor in these diagnostic assays is the specificity and affinity of the particular monoclonal antibody employed. The generation of highly specific antibodies to any of the potential indicators of impaired hemostasis is hampered by both low levels of indicators and the antigenic relatedness of the particular marker with its precursor, which is normally present at much higher levels in plasma. Examples are the formation of complexes between enzymes and their inhibitors e.g. thrombin-antithrombin III, plasmin-alpha$_2$-antiplasmin, t-PA-PAI-1. The number of new antigenic sites generated by such complex formation is extremely small and makes the production of immunological probes (such as monoclonal antibodies) difficult.

Likewise, the major problem associated with the acquisition of a monoclonal antibody to fibrin has been the structural and conformational similarities between fibrin and its physiological precursor fibrinogen. It has been estimated that the conservation of covalent structure when fibrinogen is converted to fibrin is greater that 98% (Plow, E. F., et al., *Semin. Thromb. Haemostas,* 8, 36 (1982) and, therefore, only a small percentage of the epitopes on the fibrin molecule are in fact neoantigens (and unique to fibrin). Many of the approaches which have been adopted to acquire fibrin antibodies have concentrated on immunizing animals with soluble fibrin fragments and synthetic peptides which mimic exposed neoantigenic sites on fibrin. See Hui, K. Y., et al., *Science* 22, 1129–32 (1983), Scheefers-Borchel, V., et al., *Proc. Natl. Acad. Sci USA,* 82,7091–95(1985), Elms, M. J., et al., *Thromb. Haemostas,* 50, 591–94 (1983, and Kudryk, B., et al., *Mol. Immul.,* 21, 89–94 (1984). However, it is believed that the binding site of such antibodies is conserved during the fibrin degradation process and, therefore, such antibodies also can bind to fibrin degradation products.

The subject invention permits one to take a completely different approach and utilizes the intact fibrin antigen in conjunction with the enhanced immunological sensitivity of the antigen free (AF) animal to produce a fibrin-specific monoclonal antibody. For the purpose of the subject invention, a fibrin-specific monoclonal antibody binds to fibrin and not to fibrinogen, the fibrinogen degradation products or the fibrin degradation products.

5.2. MATERIALS AND METHODS

5.2.1. ANIMALS

Germfree BALB/cAnN mice were obtained from the germfree (GF) colony maintained at the University of Wisconsin. The animals were transported to our facility under GF conditions. The Antigen-Free (AF) colony was initiated by moving pregnant GF mice fed a natural ingredient diet L-485 (See Pleasants, J. P., et al., J.Nutr. 116, 1949–1964 (1986)) to an AF isolator where the mice were immediately transferred to the chemically defined (CD) AF diet. Their offspring, which had never directly contacted a Natural Ingredient (NI) diet, were weaned from maternal milk to CD diet and were designated the first AF generation. The AF mice were mated in pairs until the female was noticeably pregnant; then the male was removed to ensure that the female would thereafter receive her full daily lipid supplement. Young were weaned at 24 days of age.

5.2.2. HOUSING

AF breeders were housed in pairs in one half of a standard polycarbonate mouse cage 28×17.8×12.7 cm. The bottom had been cut out and replaced with a false bottom of mesh stainless steel. A longitudinal divider of sheet stainless steel was bolted to the ends of the plastic cage, projecting enough above and beyond the cage to hold in place a lid of stainless wire. This recessed lid, which normally fits inside a cage, was inverted to provide more adequate head room above the false bottom. Stainless steel collars of appropriate size were welded to the top of the lid to hold 60 mL diet bottles. Four stainless steel cups were welded to the sides of the longitudinal divider at the ends, halfway between the false bottom and the top. (A picture of the cages appears in Pleasants, J. R., The germfree system for aging and immunity In: CRC Handbook of Immunology in Aging, (Kay, M. M. B. S. Makinodan, T., eds.), pp. 257–297, CRC Press, Boca Raton, Fla. (1981). The diet bottles were of brown glass. Both diet and water bottles had plastic lids with holes drilled in their centers. The bottles were filled and inverted in their collars. The lipid supplement was measured daily into the stainless steel cups. A plastic pan was placed under each cage to receive wastes.

The filter paper which served both as bedding and as ingestible fiber was Whatman ashless filter paper No. 41, purchased as clippings (Sargent Welch). For bedding the paper was cut into strips. Uncut squares of the paper were used for cleanup inside the isolator. The paper was autoclaved for 25 min at 121° C., or was irradiated (4.5 Mrad) in plastic bags. All mice received enough paper to cover one end of the cage. It was replaced when it became wet, yellow or dirty.

The cages were maintained inside a 1.37×0.6×0.6M flexible isolator of the Trexler type (Trexler, P. C., Lab. Anim. Care, 13, 572–581 (1963)), using standard gnotobiotic technology (see Wostmann, B. S., Ed., Gnotobiotes Standards and Guide Lines for the Breeding, Care and Management of Laboratory Animals, National Research Council, National Academy of Sciences, Washington, D.C.) The isolators were maintained in a room at 21° C. on a 12 h light dark schedule.

A 2.5 cm diameter Tygon tube 7.55 cm long was sealed to the top of the isolator and closed with vinyl stoppers at both top and bottom. This provided an entry for sterile filtration of diet, water and oil.

5.2.3. DIET

Table 3 indicates both diet composition and the sequence for dissolving the ingredients in ultrafiltered Milli-Q water (Millipore, Mass.). The amino acids and dextrose were Sigma tissue culture grade. Vitamins were also from Sigma except for pure retinyl palmitate, kindly supplied by Hoffman-La Roche, Inc. (Nutley, N.J.). The other reagents were Fisher certified or equivalent. The complete water soluble diet was filtered cold through an Amicon Diaflo TC3 ultrafilter using three Pm10 membranes 150 mm in diameter (Amicon).

The ultrafilter membranes had a molecular weight cut off of 10,000 daltons. The assembled ultrafilter apparatus was sterilized before use by passing a 0.15% sodium hypochlorite solution through it, followed by thorough washing. Ultrafiltered diet was stored at 4° C. in sterile reservoirs until needed. The diet was introduced into the AF isolator using a 0.2 um Nylon (MSI) filter in an autoclaved pressure filter holder with its delivery tube inserted into a No 6 Neoprene stopper. For this purpose, the upper vinyl stopper was removed from the Tygon tube sealed to the top of the isolator, and the interior of the tube was sprayed with a sterilizing solution of 2% peracetic acid containing 0.1% alkyl-aryl sulphonate. The filter holder stopper was inserted in place of the upper stopper. After 20 minutes the lower stopper was removed (inside the isolator) and diet or water was filtered into the isolator under 20 psi of nitrogen.

The composition of the lipid supplement is given in Table 4. The soy triglycerides were a preparation made from those methyl esters which vacuum distilled over a temperature range yielding the esters from palmitate to linolenate. These esters were then transesterified with glycerol to form the mixed triglycerides. (Nu-Chek Prep, Elysian, Minn.). The fat-soluble vitamins were added to the triglyceride mixture before its filtration into the isolator at which time it was warmed to 50° C. and filtered into the isolator by the same procedure used for the water-soluble portion of the diet.

The lipid intake was a measured 0.375 ml/day. Increasing the lipid supplement has greatly decreased the mortality rate of newborn mice. The average litter size has also increased to that of conventionally reared animals. Lactating females received twice the normal amount of lipid supplement.

TABLE 3

Composition and preparation of chemically defined diet L489E1Se

| Ingredient | Amount (g/100 g diet) |
|---|---|
| To 192 ml Milli-Q water 70° C. the following were added: | |
| Leucine | 1.9 |
| Phenylalanine | 0.74 |
| Isoleucine | 1.08 |
| Methionine | 1.06 |
| Tryptophan | 0.37 |
| Valine | 1.23 |
| Asparagine | 0.91 |
| Arginine HCl | 0.81 |
| Threonine | 0.74 |
| Lysine HCl | 1.77 |
| Histidine HCl.H2O | 0.74 |
| The solution was cooled to 45° C. and the following added: | |
| Glycine | 0.59 |
| Proline | 1.48 |
| Serine | 1.33 |
| Alanine | 0.59 |
| Sodium glutamate | 3.40 |
| L-tyrosine ethyl ester HCl | 0.62 |
| Ferrous gluconate | 0.05 |
| Salts 35D[1] | 0.105 |
| Sodium Selenite[2] | 0.074 |
| Solution cooled to 5° C. and the following added: | |
| Calcium glycerophosphate | 5.22 |
| Magnesium glycerophosphate | 1.43 |

TABLE 3-continued

Composition and preparation of
chemically defined diet L489E1Se

| Ingredient | Amount (g/100 g diet) |
|---|---|
| Calcium chloride $2H_2O$ | 0.185 |
| Sodium chloride-Potassium Iodide (KI) mix (containing 680 μg KI) | 0.086 |
| Vitamin B mix 111E5[3] | 0.09 |
| Vitamin B12[4] | 1.20 mg |
| Choline chloride | 0.31 |
| Potassium acetate | 1.85 |
| To 108 ml Milli-Q water at 70° C. | |
| D-Dextrose, anhydrous was added | 71.28 |

Solutions cooled to 5° C. and combined both for ultrafiltration.
[1]Composition of salts 35D mixture given in Table 5
[2]Added in addition to sodium selenite in Salts 35D
[3]Composition of vitamin B mix 111E5 (see Table 6)
[4]Added in addition to vitamin B-12 in vitamin B mix 111E5

TABLE 4

Composition of lipid supplement LADEK 69E6

| Ingredient | Amount per daily dose* (0.375 ml) |
|---|---|
| Purified soy triglycerides[1] | 0.33 g |
| Retinyl palmitate | 6.45 μg (11.7 I.U.) |
| Cholecalciferol | .0288 μg (1.15 I.U.) |
| 2 ambo-alpha-tocopherol | 3.3 mg |
| 2 ambo-alpha-tocopherol acetate | 6.6 mg |
| Phylloquinone | 72.0 μg |

*Lactating mice received twice the normal adult dose.
[1]Consisting of:
12% palmitate
1.5% stearate
24% oleate
55% linoleate
8% linolenate

TABLE 5

Composition of the 35D Salts Mixture

| Salt | Amount (mg/100 g) |
|---|---|
| $Mn(acetate)_2\ 4H_2O$ | 55.4 |
| $ZnSO_4\ H_2O$ | 40.6 |
| $Cu(acetate)_2\ H_2O$ | 3.7 |
| $Cr(acetate)_3\ H_2O$ | 2.5 |
| NaF | 2.1 |
| $SnSO_4\ 2H_2O$ | 0.37 |
| $(NH_4)_6\ Mo_7O_{24}\ 4H_2O$ | 0.37 |
| $NiCl_2\ 3H_2O$ | 0.37 |
| $Co(acetate)_2\ 4H_2O$ | 0.11 |
| $Na_3VO_4$ | 0.22 |
| $Na_2SeO_3$ | 0.096 |

TABLE 6

Composition of the Vitamin B Mixture 111E5

| Ingredient | Amount (mg/100 g) |
|---|---|
| Thiamine HCl | 1.23 |
| Pyridoxine HCl | 1.54 |
| Biotin | 0.25 |
| Folic Acid | 0.37 |
| Vitamin B12 | 0.37 |
| Riboflavin | 1.85 |
| Niacinamide | 9.2 |
| i-inositol | 61.9 |
| Calcium pantathenate | 12.3 |

Water was Milli-Q ultrafiltered grade and was filtered into the isolator in the same manner as the diet.

5.2.4. MICROBIOLOGICAL MONITORING

The antigen-free system was tested for microbial contamination according to guidelines set out in Wostmann, B. S. ed. (1970) Gnotobiotics Standards and guidelines for the breeding care and management of laboratory animals, National Research Council, National Academy of Sciences, Washington, D.C. Briefly, swabs wetted with diet and water from inside the isolator were used to obtain fecal smears obtained fresh from the mouse and from the accumulated waste under each cage. Smears were also taken from the walls of the isolator particularly around the entry ports. Duplicate smears were always taken. One set was tested by direct microscope examination for bacteria and fungi, using a gram stain. The second set of swabs was used for detection of microorganisms. Three weeks were allowed to elapse before a culture was considered to be negative.

Microbiological testing was performed approximately every two weeks or a few days after a new entry to the isolator had been made.

5.3. THE PRODUCTION OF MONOCLONAL ANTIBODIES USING ANTIGEN-FREE MICE

The antigen-free mice described hereinabove were used as the lymphocyte donor in the production of monoclonal antibodies. Solutions of all antigens were prepared under sterile conditions in a laminar flow hood.

The following protocol was adopted for the immunization of the AF mice. The antigen (25–50 micro g) was dissolved in sterile saline (100 micro 1) and emulsified with an equal volume of Freund's Complete Adjuvant (FCA). Interferon (1000 units) was added to the solution of antigen prior to the preparation of the emulsion. Sterile syringes and needles were used for all immunizations. The syringes were transferred to the AF isolator via the entry port where they were sterilized by spraying with a solution of peracetic acid (2%). Booster injections were given using the same amount of antigen and the replacement of FCA with Freund's Incomplete Adjuvant. A total of three booster immunizations were given each at intervals of three weeks. The final boost (without adjuvant) was given 4–7 days prior to fusion. All immunizations were given intraperitoneally. The mice were removed from the isolator on the day of the fusion and were immediately sacrificed by $CO_2$ asphyxiation. The spleens were removed and the splenocytes fused with mouse myeloma cells (NS1) using standard hybridoma technology.

5.4. USE OF THE ANTIGEN-FREE ANIMAL SYSTEM FOR THE PRODUCTION OF A FIBRIN-SPECIFIC MONOCLONAL ANTIBODY

The antigen-free system was used to generate a fibrin-specific monoclonal antibody. The antibody is highly specific and does not recognize fibrinogen, fibrin degradation products or fibrinogen degradation products. The hybridoma cell line was produced by fusion of splenocytes from antigen free BALB/c mice, immunized with human fibrin, and NS1 myeloma cells.

5.4.1. IMMUNIZATION SCHEDULE

Three eight week old female antigen free mice were immunized with 33 micrograms of a human fibrin preparation. The preparation was a freeze fracture sample of fibrin which was prepared as follows:

Human fibrinogen was converted to fibrin by thrombin and Factor XIIIa. The fibrin clot was then frozen in liquid nitrogen and reduced to an extremely fine powder by mechanical disruption. A dispersion of the freeze fractured fibrin was made in saline to give a clear solution of crosslinked fibrin XL-Fn with a final concentration of 1 mg/mL. 33 microL of this fibrin antigen was used to immunize the animals. The volume of the antigen solution was adjusted to 100 microL with sterile saline and was then emulsified with FCA as described in the last section. Two booster immunizations were administered, at intervals of three weeks, using the same level of antigen in Freund's Incomplete Adjuvant. The final booster was given 4 days prior to the fusion. The same level of antigen was used and adjuvant was replaced with saline.

5.4.2. DETECTION AND DETERMINATION OF ANTIBODY

Qualitative and quantitative determinations of monoclonal antibody were performed using an enzyme linked immunosorbent assay (ELISA). The ELISAs were performed using human fibrin immobilized onto a 96 well PVC plate (Costar). The fibrin coated assay plates were prepared by incubating 100 microL of a fibrinogen solution (Kabi, grade L) (50 micrograms/mL borate/saline buffer) overnight at 4° C. Unbound fibrinogen was removed by washing with PBS containing 0.05% TWEEN™ 80 (PBS-dispersant TWEEN). The fibrinogen coated onto each plastic well was converted to fibrin by incubation with 100 microliters of a thrombin solution (10 NIH units/ml) containing 2 mM $CaCl_2$ for 1 hour at 37° C. Standard calibration curves for the antibody were constructed using a preparation of antibody which was homogeneous by SDS-PAGE.

To prevent non-specific binding, the fibrin coated plates were incubated with a 1% solution of BSA in PBS pH7.4. Antibody containing solutions (100 microL) were then added and incubated at 37° C. for 90 minutes. After each step in the procedure the wells were extensively washed with PBS-Tween. Bound antibody was detected by the addition of a 1000 fold dilution of rabbit anti-mouse antibody conjugated to alkaline phosphatase (Sigma) diluted in PBS, 1% BSA pH8.0.

5.4.3. PRODUCTION OF HYBRIDOMAS-FUSION

The mice were sacrificed by $CO_2$ asphyxiation and a splenectomy performed immediately. The spleen cells from the immunized mice were fused with the fusagent polyethylene glycol 4000 (3000–3700). The cells were incubated in HAT selection media in T flasks for 1 week. After this time the cells were plated out into 5×96 well plates from which 93 wells showed growth. Of these, 19 wells were positive for the fibrin antigen. One of these clones, F492D8 (later renamed MH1), produced antibody which recognized the fibrin antigen but did not crossreact with fibrinogen. This particular clone, MH1, was recloned three times by limiting dilution with the tertiary cloning phase performed at 1 cell per well. Once the cell line was stabilized it was weaned onto a serum-free medium. The cell line produces antibody at the level of approximately 7.5 mg/liter.

5.4.4. PURIFICATION OF MONOCLONAL ANTIBODY

Before purification (4 Liter batches of) tissues culture supernatants were centrifuged to remove cellular debris and filtered through a 0.8 micro nylon membrane to remove any residual particulate material. The hybridoma supernatant was concentrated at 4° C. to a volume of 500 mL using a spiral wound ultrafiltration system employing a YM type membrane (Amicon) with molecular weight cutoff 30,000. Buffer exchange to 20 mM 2(N-morpholine) ethane sulphonic acid (MES), pH6 (Buffer A) was accomplished by diafiltration according to the manufacturers instructions. After further concentration to a final volume of 100 ml, the antibody solution was filtered through a 0.451 micron nylon membrane before further purification. The concentrated antibody solution was purified by liquid chromatography on a Waters HPLC chromatograph using a 7.75 mm×10 cm ABx column (J. T. Baker, Phillipsburg, N.J.). The column was equilibrated with buffer A and the sample (100 ml) was applied at a flow rate of 1.0 ml/min. After extensive washing with buffer A the antibody was eluted from the column with a gradient from buffer A to 100% buffer B (1M sodium acetate pH7) at 1 ml/min. Fractions (2 ml) were collected and those containing MAb (as determined by ELISA) were pooled and dialysed against phosphate buffer saline (PBS) (20 mM sodium phosphate, 150 mM sodium chloride, pH7.4) and stored at −20° C. at concentrations>1 mg/ml. The ABx column was regenerated by washing for 5 minutes with 100% buffer B, followed by re-equilibration with 15 column volumes of buffer A.

5.5. DETERMINATION OF FIBRIN SPECIFICITY

Initial determination of fibrin specificity was achieved by screening hybridoma supernatants separately on fibrin and fibrinogen coated microtiter plates. Only those cell lines producing antibody that did not crossreact with fibrinogen were accepted.

Further confirmation of fibrin specificity was determined utilizing a competition assay with fibrinogen in solution, thereby confirming that the antibody does not recognize fibrinogen in solution.

The competition assay employed to ascertain the fibrin specificity of the antibody was performed as described for the ELISA assay hereinabove with preincubation of the antibody with fibrinogen in solution. Briefly, hybridoma supernatant was incubated at 37° C. for 30 minutes with solutions of fibrinogen at physiological concentrations (4 mg/ml) containing BSA (10 mg/ml) to prevent non specific binding of antibody to fibrinogen. The fibrinogen/antibody solution was then transferred to wells of a microtiter plate which had been coated with fibrin. GlyProArgPro (GPRP) was added to the fibrinogen inhibitor to prevent possible polymerization of fibrinogen by residual thrombin in the fibrin wells. The assay was then performed as a conventional ELISA assay for antibody bound to an immobilized antigen. In all experiments to test the fibrin specificity of the MH1 antibody a second antibody 45J was used as a control. 45J crossreacts with fibrin and fibrinogen.

5.5.1. DETERMINATION OF CROSSREACTIVITY WITH FIBRINOGEN

5.5.1.1. IMMOBILIZED FIBRIN AND FIBRINOGEN

The cell line MH1 produces a murine monoclonal antibody which crossreacts with fibrin when it is immobilized on the surface of a PVC microtiter assay plate (Table 7). In the same assay the antibody does not recognize fibrinogen immobilized on the plate. As the data on table 7 indicate, there is a dramatic increase in immunoreactivity once fibrinogen is converted to fibrin by thrombin, indicating clearly the exposure or formation of a neoepitope on the fibrin molecule. The control antibody, 45J, however clearly recognizes an epitope which is conserved when fibrinogen is converted to fibrin.

5.5.1.2. COMPETITION ASSAY WITH FIBRIN AND FIBRINOGEN

The fibrin specificity of the, MH1 antibody was further demonstrated in a competition assay in which hybridoma supernatant was preincubated with a fibrinogen solution (final concentration of 4 mg/ml) prior to an ELISA on fibrin coated wells. Since such a high level of fibrinogen was used in this competition assay (×500 that of the antibody concentration) BSA (10 mg/ml final concentration) was added to the mixture. The peptide GPRP was added to prevent fibrin polymerization by residual thrombin on the fibrin coated wells. The results of this assay indicate that the MH1 antibody does not recognize fibrinogen in solution (Table 8).

Assuming 400 ng. of fibrin binds to each well of the microtiter assay plate, then the fibrinogen level used in this particular competition assay represents a 1,000 fold excess over the bound fibrin antigen. In addition it represents a 400 fold excess of the antibody level in the tissue supernatant.

TABLE 7

Crossreactivity of MH1 Antibody with Fibrinogen and Fibrin Antigen $A_{405nM}$/30 min.

| MAb | Fibrin | Fibrinogen |
|---|---|---|
| MH1 | .90 | .025 |
| 45J | 1.65 | 1.50 |

TABLE 8

Crossreactivity of MH1 Antibody with Fibrin in the Presence of Fibrinogen $A_{405\ nm}$/30 min.

| MAb | +fibrinogen | −fibrinogen |
|---|---|---|
| MH1 | 1.24 | 1.27 |
| 45J | 0.438 | 1.74 |

5.5.2. DETERMINATION OF CROSSREACTIVITY WITH FIBRIN(OGEN) DEGRADATION PRODUCTS

Fibrinogen degradation products (FDPs) were prepared by incubating fibrinogen with plasmin at 37° C. for time periods ranging from 10 minutes to 3 hours. At the desired time fibrinogenolysis was stopped by the addition of Trasylol (100 Kallikrein inhibitor units/mL) and 20 mM epsilon amino caproic acid (EACA).

Crosslinked fibrin degradation products (XLFDPs) were prepared by the addition of thrombin (4NIH units/mL) to a fibrinogen solution (5 mg/mL) in Tris buffered saline (TBS, pH 7.4, 50 mM Tris HCl, 150 mM NaCl) containing 10 mM $CaCl_2$, plasminogen (0.25 mg/mL) and urokinase (50 IU/mL). The mixture was incubated at 37° C. and the plasmin digestion terminated at different time intervals as described herein-above for the FDPs.

To determine crossreactivity of the antibody with fibrin degradation products and fibrinogen degradation products the appropriate degradation products were coated onto microtiter plates and ELISAs were performed by conventional methods. As the results in Table 9 indicate, the MH1 antibody does not crossreact with any plasmin generated fibrinogen degradation products. As table 10 indicates, the antibody does not react with XL-fibrin degradation products. This observation also was made when the antibody was tested for crossreactivity by Western blotting analysis.

The conclusion can be drawn that the antibody recognizes an epitope of the intact fibrin molecule which is not present or exposed on the surface of the precursor molecule, fibrinogen. The epitope is apparently destroyed by plasmin digestion of crosslinked fibrin as the data in table 8 suggest.

Accordingly, the MH1 antibody is a fibrin-specific monoclonal antibody which can be defined as follows:

For the purpose of the subject invention a fibrin-specific monoclonal antibody is a monoclonal antibody that:

1. in a competition assay to measure crossreactivity with fibrin and fibrinogen, as described hereinabove, the monoclonal antibody has less than about 75%, and preferably less than about 10%, crossreactivity with fibrinogen when fibrinogen is utilized in a quantity of a 1,000 fold excess as compared to fibrin, 2. in an assay to measure crossreactivity with crosslinked fibrin and fibrin degradation products, as described hereinabove, the reactivity of the monoclonal antibody with the fibrin that has been digested with plasmin for about three hours is less than about 50%, and preferably less than about 40%, of the reactivity of the monoclonal antibody with fibrin at time zero, and 3. in an assay to measure crossreactivity with fibrinogen and fibrinogen degradation products, as described hereinabove, the reactivity of the monoclonal antibody with fibrinogen that has been digested with plasmin for about four hours is no greater than the reactivity of the monoclonal antibody with fibrinogen at time zero.

The MH1 antibody has been further characterized by determining its affinity for fibrin. The affinity was determined by Scatchard analysis (Frankel et al., *Molecular Immunology*, 16, 101–106(1979)) using 125I labelled MH1 antibody. The value obtained for the dissociation constant $K_D$ was $6.7 \times 10^{-10}$M. Such affinity is about 5,000 times that of the affinity of t-PA for fibrin.

It has also been determined by Western Immunoblotting analysis that the MH1 antibody does not crossreact with the Aα, Bβ or gamma chains of fibrinogen. Also, it has been determined by the same method of analysis that the MH1 antibody does not crossreact with thrombin treated Aα or Bβ chains of fibrinogen. (Thrombin treatment of fibrinogen results in the release of fibrinopeptide A and fibrinopeptide B from the Aα chain and Bβ chain, respectively, therefore forming the α chain and β chain of fibrin.)

TABLE 9

Crossreactivity of MH1 Antibody
with Fibrinogen Degradation Products

| Plasmin Digestion Time (mins) | $A_{405\ nm/30\ min}$ MH1 | 45J |
|---|---|---|
| 0 | 0.15 | 1.037 |
| 10 | 0.10 | nm |
| 20 | 0.11 | 1.02 |
| 40 | 0.11 | 0.410 |
| 60 | 0.10 | 0.330 |
| 240 | 0.09 | 0.300 |

TABLE 10

Crossreactivity of MH1 Antibody
with Fibrin Degradation Products

| Plasmin Digestion Time (hours) | $A_{405\ nm/30\ min}$ MH1 | 45J |
|---|---|---|
| 0 | 0.890 | 1.40 |
| 3 | 0.354 | 1.0 |
| 5 | 0.310 | 0.77 |

In addition, as the results in Table 9 indicate, the control antibody, 45J antibody, binds to fibrinogen and does not crossreact with fibrinogen degradation products. Accordingly, such a monoclonal antibody is a fibrinogen-specific monoclonal antibody and represents another aspect of the subject invention. The fibrinogen-specific monoclonal antibody can be utilized in any immunoassay that can be utilized to determine plasma fibrinogen levels in vitro. The 45J antibody has been further characterized in that it has been determined that the 45J epitope is on the α chain of fibrinogen in the region from about amino acid 206 to about 424 and most likely in the region from about amino acid 207 to about 231. For the purpose of the subject invention, a fibrinogen-specific monoclonal antibody is an antibody that in an assay to measure crossreactivity with fibrinogen and fibrinogen degradation products, as described hereinabove, the reactivity of the monoclonal antibody with fibrinogen that has been digested with plasmin for about 40 minutes is less than about 50% of the reactivity of the monoclonal antibody with fibrinogen at time zero.

The 45J hybridoma was made by conventional techniques utilizing a conventional Balb/c mouse wherein the mouse was immunized with fibrin. However, fibrinogen also can be utilized as the antigen.

5.5.3. DETERMINATION OF CROSS REACTIVITY WITH NONCROSSLINKED FIBRIN AND NONCROSSLINKED FIBRIN CLOTS

It has been demonstrated by ELISA that the antibody MH1 crossreacts with not only crosslinked fibrin (XLFn) but also noncrosslinked fibrin (NONXLFn). The ELISA was performed as follows:
1. 96 well microtiter assay plates were coated with 100 ul of a fibrinogen solution (50 ug/mL in borate (pH8.5) saline buffer) at 4° C. overnight.
2. Crosslinked fibrin was formed in the fibrinogen coated wells by incubation for 1 hour at 37° C. with a thrombin solution (10NIH units/ml) in Tris buffered saline (TBS, pH 7.4, 50 mM Tris HCl, 150 mM NaCl), containing 2 mM $CaCl_2$ and 10 mM cysteine.
3. Noncrosslinked fibrin was formed in the fibrinogen coated wells by incubation for 1 hour at 37° C. with a thrombin solution (10 NIH units/ml) in phosphate buffer (pH 6.1) containing EDTA to a final concentration of 0.0125M.
4. The bound antibody was determined by incubation with an antimouse alkaline phosphatase conjugate. Bound conjugate was determined by the addition of an alkaline phosphatase substrate and the resultant colorimetric reaction monitored at 405 nM in an automatic plate reader.

The results of the assay are shown in Table 11 and it can be concluded that the antibody crossreactivity with crosslinked fibrin is greater than it is with noncrosslinked fibrin. The simplest explanation being that the covalent crosslinking present in the crosslinked polymeric structure serves to lock or freeze the conformation which the antibody recognizes. In the noncrosslinked species the conformation, although it is formed, it is not stabilized by covalent bonding of the polymer.

It has also been demonstrated that the antibody crossreacts with both crosslinked and noncrosslinked clots, formed in vitro. Crosslinked fibrin was prepared by incubating a fibrinogen solution (In Tris (50 mM, pH7.4) saline, containing $CaCl_2$ (2 mM) and cysteine (10 mM)) with thrombin (10NIH units/ml) for 3 hours at 37° C. The non-crosslinked fibrin was formed by incubating a fibrinogen solution (3 mg/ml) in phosphate buffer (pH6.1) containing EDTA to a final concentration of 0.0125M with a thrombin solution (10NIH units/ml) for 3 hours at 37° C. After formation of the clots, they were washed and incubated at 37° C. with 400 ul of a 1% BSA solution containing $^{125}$Iodine-labelled MH1 antibody. Small aliquots of solution were removed at different time points and the amount of antibody uptake was determined by counting the plasma in a gamma counter.

Table 12 shows the uptake of antibody by both the noncrosslinked and crosslinked clots.

TABLE 11

Crossreactivity of MH1 Antibody with Crosslinked and Noncrosslinked Fibrin

| Antibody Concentration (ng./ml.) | Crosslinked Fibrin | Noncrosslinked Fibrin |
|---|---|---|
| | (Absorbance at 405 nanometers) | |
| 100.000 | 0.764 | 0.409 |
| 50.000 | 0.460 | 0.319 |
| 25.000 | 0.305 | 0.154 |
| 12.500 | 0.174 | 0.074 |
| 6.250 | 0.069 | 0.000 |

TABLE 12

Crossreactivity of MH1 Antibody with Crosslinked and Noncrosslinked Fibrin Clots

| Fibrin Clot | % Uptake of Labelled Antibody After 8 Hours |
|---|---|
| Crosslinked | 79% |
| Noncrosslinked | 76% |

5.6. DEPOSIT OF HYBRIDOMA

MH1 and 45J were deposited in the American Type Culture Collection (ATCC) on Jun. 9, 1988 and given accession number HB 9739 and HB 9740, respective. The ATCC is located at 10801 University Boulevard Manassas, Va. 20110-2209. MH1 antibody is an $IgG_1$ antibody with a kappa light chain and it has been observed that the MH1 antibody crossreacts with not only human fibrin but also rabbit fibrin.

The subject invention is not intended to be limited in scope to the hybridomas deposited but they are intended as a single illustration of hybridomas that produced a fibrin-specific monoclonal antibody and a fibrinogen-specific monoclonal antibody, as defined herein. Any cell line that is functionally equivalent is within the scope of the subject invention. By the term "functionally equivalent" it is meant that an antibody is capable of competing with the MH1 antibody or 45J antibody in binding to the epitope of fibrin to which the MH1 antibody binds or to the epitope of fibrinogen to which the 45J antibody binds, respectively. In addition, such term includes fibrin-specific monoclonal antibodies and fibrinogen-specific monoclonal antibodies, as defined herein, that bind to an epitope different from that which the MH1 antibody binds and the 45J antibody binds, respectively.

5.7. IN VIVO DIAGNOSTIC AND THERAPEUTIC USES FOR FIBRIN-SPECIFIC MONOCLONAL ANTIBODIES

5.7.1. CLOT/VASCULAR DISEASE LOCALIZATION

The fibrin-specific monoclonal antibodies of this invention are capable of targeting fibrin clots or aggregation of fibrin in vivo. They can, therefore, be used in humans for localization of possible tissue or vascular damage and for monitoring of vascular diseases. A fibrin-specific monoclonal antibody is particularly preferred for this use because such monoclonal antibody will not bind to fibrinogen, fibrin degradation products and fibrinogen degradation products, thereby reducing background, which permits one to more precisely localize the fibrin clot or aggregation of fibrin.

For this application, it is preferable to use purified monoclonal antibodies. preferably, purification may be accomplished by HPLC methods. Purification of monoclonal antibodies for human administration may also be accomplished by ammonium sulfate or sodium sulfate precipitation followed by dialysis against saline and filtration sterilization. Alternatively, immunoaffinity chromatography techniques may be used to purify the monoclonal antibodies.

The purified monoclonal antibodies can be labelled with radioactive compounds, for example $^{123}I$, $^{125}I$, $^{131}I$, $^{99}mTc$, $^{111}In$, and administered to a patient intravenously. The antibody also can be labelled with a magnetic probe. NMR can then be utilized to pinpoint the clot. After localization of the antibodies at the clot or fibrin aggregation they can be detected by emission tomographical and radionuclear scanning techniques thereby pinpointing the location of, for example, the thrombus or fibrin encapsulated tumor.

By way of illustration, the purified monoclonal antibody is suspended in an appropriate carrier, e.g., saline, with or without human albumin, at an appropriate dosage and is administered to a patient. The monclonal antibodies are preferably administered intravenously, e.g., by continuous intravenous infusion over several hours.

5.7.2. TREATMENT OF VASCULAR DISEASES WITH MONOCLONAL ANTIBODY CONJUGATES

The monoclonal antibodies of this invention can be used in conjunction with a broad range of pharmaceutical agents such as cytotoxic reagents and thrombolytic reagents, e.g. t-PA, urokinase streptokinase, and other proteases that are capable of lysing fibrin. Such use is particularly preferred because the fibrin-specific monoclonal antibodies of the subject invention permit a very efficient use of such reagents because none of the reagent will be lost by binding to fibrinogen, fibrin degradation products or fibrinogen degradation products. For various reviews on the subject, see Bale et al., 1980, Cancer Research, 40:2965–297; Ghose and Blair, 1978, J. Natl. Cancer Inst., 61(3):657–676; Gregoriadis, 1977, Nature, 265:407–411; Gregoriadis, 1980 Pharmac. Ther., 10:103–108; and Trouet et al., 1980, Recent Results Cancer Res., 75:229–235.

The methods used for binding these agents to the monoclonal antibody molecule can involve either non-covalent or covalent linkages. Since non-covalent bonds are more likely to be broken before the antibody complex reaches the target site, covalent linkages are preferred. For instance, a carbodiimide bond can be formed between the carboxy groups of the pharmaceutical agent and the amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde which is then reacted with the antibody molecule. Attachment occurs via formation of a Schiff base with amino groups of the antibody molecule. Additionally, drugs with reactive sulfhydryl groups have been coupled to antibody molecules.

6. IN VITRO DETECTION AND MEASUREMENT OF SOLUBLE FIBRIN

6.1 BACKGROUND

As described above, see Section 5.1, the hemostatic mechanism involves a complex sequence of reactions, by which fibrinogen is ultimately converted by thrombin to fibrin. The end result of these reactions is the formation of a thrombus (blood clot). The sequence of reactions may be simply represented by a three step process as follows:

Step 1—Proteolysis: Fibrinogen Thrombin→Fibrin Monomers+Fibrinopeptides A and B

Step 2—Polymerization: Fibrin monomers⇌Soluble Fibrin Polymers

Step 3—Clotting: Soluble Fibrin Polymers→Fibrin Clot

Fibrinogen is composed of three pairs of non-identical polypeptide chains: $A\alpha$, $B\beta$ and $\gamma$. See L. Stryer, Biochemistry, Third Edition p. 249, W. H. Freeman and Company New York (1988). In the initial step, whereby fibrinogen is converted to fibrin, shown above as step 1, fibrinogen is cleaved by thrombin to release fibrinopeptide A from the amino-terminal ends of the two fibrinogen A$\alpha$-chains. The resultant monomer is the DesAA fibrin monomer. As also shown above in step 1, simultaneously, but more slowly, thrombin also cleaves fibrinopeptide B from the amino-terminal ends of the two fibrinogen B$\beta$-chains. As a result of the fibrinopeptide release, new amino-terminals are exposed on the fibrin $\alpha$ and $\beta$ chains. As depicted above, the molecules formed in step 1 are fibrinopeptide A, fibrinopeptide B, and the fibrin monomers DesAA fibrin monomer, and DesAABB fibrin monomer, shown above as "fibrin monomers". See W. Nieuwenhuizen, Blood Coagulation and Fibrinolysis, 4:93–96 (1993). As shown above in step 2, the fibrin monomers then form both non-covalent (non-crosslinked) and covalent (crosslinked) polymers to form soluble fibrin polymers. As shown above in step 3, the soluble fibrin polymers then form the fibrin clot.

Soluble fibrin is defined as any molecular species originating from fibrinogen or fibrin that can lead to fibrin polymer formation or any fibrin(ogen) derived molecular species which has a molecular weight greater than the molecular weight of native fibrinogen, and is maintained in solution in blood. Non-crosslinked and crosslinked DesAABB fibrin polymers, formed in step 2 above, are two of the several species of soluble fibrin and are also two species of soluble fibrin polymer. Additionally, the term soluble fibrin includes various other species; for example, DesAA fibrin polymers, complexes formed by interactions between fibrin monomers (either DesAA or DesAABB fibrin monomers) and the fibrinogen degradation products X, Y, D and E (see Section 5.1 above for a description of these degradation products) and also, for example, DesAA and DesAABB monomers in complex with fibrinogen, see Nieuwenhuizen, pp. 93–94.

Soluble fibrin polymers are the immediate precursors of the insoluble fibrin, i.e., the clot, and consequently the plasma levels of the soluble fibrin polymers are believed to be elevated in individuals with impending or existing thrombosis (intravascular blood clot formation). The detection and measurement of the amount of these polymers in blood, in particular the DesAABB soluble fibrin polymers would therefore, be useful as an indication of incipient blood clot formation. See Bang and Chang, pp. 119–121, and Nieuwenhuizen, p. 94, Marder et al. U.S. Pat. No. 5,206,140.

Certain species of soluble fibrin have previously been detected or measured and detected using a variety of methods including, for example, measurement of fibrinopeptide A, measurement by using antibodies to the Aα and γ epitopes exposed upon conversion of fibrinogen to fibrin, Nieuwenhuizen, 94–96, and measurement of D-dimers, Marder et al. U.S. Pat. No. 5,206,140. Other methods used to detect or measure and detect soluble fibrin include measurement of agglutination of erythrocytes coated with fibrin in the presence of soluble fibrin, gel exclusion chromatography, rate enhancement of plasminogen activation by the plasminogen activator t-PA, see Nieuwenhuizen, at p. 94, ethanol or protamine sulfate gelation, N-terminal analysis of fibrinogen fractions purified from plasma, incorporation of $^{14}$C-labeled glycine-ethyl ester and agarose gel chromatography, see Bang and Chang at pp. 111–118. None of these tests detects and measures specifically both soluble crosslinked and soluble non-crosslinked fibrin polymers.

6.2 IN VITRO ASSAY FOR SOLUBLE CROSSLINKED FIBRIN POLYMERS AND SOLUBLE NON-CROSSLINKED FIBRIN POLYMERS

The present invention is based upon the discovery that it is possible to provide an in vitro assay to detect and measure the amount of soluble crosslinked DesAABB fibrin polymers and soluble non-crosslinked DesAABB fibrin polymers, which polymers are composed of DesAABB fibrin monomers, in an assay system wherein there is no detection of (a) fibrinogen, (b) fibrinogen degradation products, (c) DesAA fibrin monomers, (d) DesAA fibrin polymers, (e) DesAABB fibrin monomers, (f) crosslinked fibrinogen (Factor XIIIa treated fibrinogen), (g) DesAA fibrin monomer-fibrinogen complexes and (h) fibrin degradation products ("species (a)–(h)"). The fibrinogen degradation products and the fibrin degradation products are those generated by plasmin digestion of fibrinogen or fibrin as described in Section 5.5.2 above.

It is believed that the above described assay is particularly useful in the clinical diagnosis of conditions characterized by thrombosis.

The assay may be carried out utilizing any suitable sample of body fluid but is preferably done utilizing as a sample mammalian blood. Suitable mammals include for example rabbits, monkeys, and humans with humans being most preferred.

In such in vitro assays, any means, known or to be developed, of detecting soluble crosslinked DesAABB fibrin polymers and soluble non-crosslinked DesAABB fibrin polymers which means does not detect species (a)–(h) can be utilized. Once detected, the soluble crosslinked DesAABB fibrin polymers and soluble non-crosslinked DesAABB fibrin polymers in a sample can be measured either by comparison to a control sample or by use of standards having known amounts of soluble crosslinked DesAABB fibrin polymers and soluble non-crosslinked DesAABB fibrin polymers which standards contain none of species (a)–(h).

It is to be noted that a means of detection is any means by which one is able to determine the presence of the material of interest in a sample. A preferred means of detection is an antibody to the soluble crosslinked DesAABB fibrin polymers and the soluble non-crosslinked DesAABB fibrin polymers, which antibody does not cross-react with (a) fibrinogen, (b) fibrinogen degradation products, (c) DesAA fibrin monomers, (d) DesAA fibrin polymers, (e) DesAABB monomers, (f) crosslinked fibrinogen, (g) DesAA fibrin monomer-fibrinogen complexes and (h) fibrin degradation products. Said antibody can be used to detect and measure the amount of soluble crosslinked DesAABB fibrin polymer and soluble non-crosslinked DesAABB fibrin polymer in a sample. Such antibodies include polyclonal or monoclonal antibodies, preferably monoclonal. The antibody can be derived from any species. Preferably, however, the antibody is of human or murine, or rabbit origin. In addition, such antibodies include, but are not limited to chimeric antibodies, single chain antibodies, and Fab fragments.

An example of such antibody is the monoclonal antibody MH1, described in sections 5.5.1–5.5.3, and also section 5.6 above. It is believed that MH1, in addition to having the above described binding characteristics, also does not bind to the fibrinogen-fibrin degradation product complex. This characteristic of MH1 may enhance its efficacy as a means of detecting and measuring soluble crosslinked and soluble non-crosslinked DesAABB fibrin polymers.

It is to be noted that two or more antibodies can be used as the means of detection. Thus, antibodies with different specificities can be used in combination to detect and measure soluble crosslinked DesAABB fibrin polymers and soluble non-crosslinked DesAABB fibrin polymers in a sample, wherein for example, neither antibody alone is able to form a complex with both soluble crosslinked DesAABB fibrin polymers and soluble non-crosslinked DesAABB fibrin polymers, whereas the two or more antibodies can form such complexes. Of course, no one antibody can crossreact with species (a)–(h).

It is also to be noted that when antibodies are used it may be necessary to utilize a species specific antibody.

For the production of antibodies, various host animals can be immunized by injection with soluble crosslinked DesAABB fibrin polymers and soluble non-crosslinked DesAABB fibrin polymers as the antigen, including but not limited to rabbits, mice, rats, etc. Such polymers can be selectively isolated using, for example, the MH1 antibody, coupled to a SEPHAROSE™ gel MH1 antibody affinity column. Such polymers can be prepared as follows: Soluble fibrin can first be prepared in vitro by addition of low levels of thrombin to citrated plasma. After quenching of the thrombin activity by addition of a potent thrombin inhibitor such as hirudin, the plasma samples may be applied to a SEPHAROSE™ gel-MH1 column. Such MH1 column may be prepared by the coupling of MH1 antibody to cyanogen bromide activated SEPHAROSE™ 4B gel (Pharmacia) as is known in the art. See Pharmacia product insert for methods for preparing an antibody-Sepharose 4B column using pre-activated SEPHAROSE™ 4B gel. The soluble fibrin is initially applied to the SEPHAROSE™ gel-MH1 column in the presence of phosphate buffered saline (PBS). After binding to the SEPHAROSE™ gel-MH1 column, in the presence of (PBS) the soluble fibrin binding to the MH1-Sepharose may be eluted using a solution of sodium thiocyanate. After dialysis against PBS, the soluble fibrin polymer which has been isolated may be stored at −70° C.

Various adjuvants can be used in conjunction with the isolated polymers to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *corynebacterium parvum*.

Monoclonal antibodies specific for soluble crosslinked and soluble non-crosslinked DesAABB fibrin polymers which antibodies do not cross react with species (a)–(g) can be prepared by using any technique which provides for the production of antibody molecules by continuous cell lines in culture. These include but are not limited to the hybridoma technique originally described by Kohler and Milstein, (*Nature*, 1975, 256:495–497), the more recent human B-cell hybridoma technique (Kosbor et al., 1983, *Immunology Today*, 4:72) and the EBV-hybridoma technique (Cole et al., 1985, *Monoclonal Antibodies and Cancer Therapy*, Alan R. Liss, Inc., pp. 77–96). In an additional embodiment of the invention monoclonal antibodies can be produced in germ-free animals utilizing recent technology, see sections 5.2–5.4. An example of the production of such antibody is the production of MH1 described above in sections 5.3–5.6.

According to the invention, human antibodies can be used and can be obtained by using human hybridomas (Cote at al., 1983, *Proc. Natl. Acad. Sci.*, 80:2026–2030) or by transforming human B cells with EBV virus in vitro (Cole et al., 1985, in, *Monoclonal Antibodies and Cancer Therapy*, Alan R. Liss, pp. 77–96). In fact, according to the invention, techniques developed for the production of "chimeric antibodies" (Morrison et al., 1984, *Proc. Natl. Acad. Sci.*, 81:6851–6855; Neuberger et al., 1984, *Nature*, 312:604–608; Takeda et al., 1985, *Nature*, 314:452–454) by splicing the genes from a mouse antibody molecule of appropriate antigen specificity together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce specific single chain antibodies.

An additional embodiment of the invention utilizes the techniques described for the construction of Fab expression libraries (Huse et al., 1989, *Science*, 246:1275–1281) to allow rapid and easy identification of monoclonal Fab fragments with the desired specificity to soluble crosslinked and soluble non-crosslinked DesAABB fibrin polymers.

Antibody fragments which contain specific binding sites for soluble crosslinked and soluble non-crosslinked DesAABB fibrin polymers may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

The antibodies of the present invention may be used in any immunoassay system known in the art including, but not limited to: radioimmunoassays, enzyme-linked immunosorbent assays, "sandwich" assays, precipitin reactions, gel diffusion immunodiffusion assays, agglutination assays, fluorescent immunoassays, protein A immunoassays and immunoelectrophoresis assays, to name but a few. U.S. Pat. No. 4,629,783 and patents cited therein also describe suitable assays.

The antibodies may be used as the basic reagents in a number of different immunoassays to determine the presence of the soluble crosslinked and soluble non-crosslinked DesAABB fibrin polymers in a sample of blood or other body fluid. Generally speaking, the antibodies can be employed in any type of immunoassay, whether qualitative or quantitative. This includes both the two-site sandwich assay and the single site immunoassay of the non-competitive type, as well as traditional competitive binding assays.

Particularly preferred, for ease of detection, and its quantitative nature, is the sandwich or double antibody assay, of which a number of variations exist, all of which are intended to be encompassed by the present invention.

For example, in a typical forward sandwich assay, unlabeled antibody is immobilized on a solid substrate, e.g., microtitre plate wells, and the sample to be tested is brought into contact with the bound molecule. After a suitable period of incubation, for a period of time sufficient to allow formation of an antibody-antigen binary complex, a second antibody, labelled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with control samples (standards) containing known amounts of antigen. Variations on the forward sandwich assay include the simultaneous assay, in which both sample and antibody are added simultaneously to the bound antibody, or a reverse sandwich assay in which the labelled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid to be tested is then added to the solid phase complex and incubated for a period of time sufficient to allow binding of any soluble non-crosslinked DesAABB fibrin polymer and soluble crosslinked DesAABB fibrin polymer present to the antibody specific for the above proteins. The second antibody is then added to the solid phase complex and incubated for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labelled antibody is added to the first antibody complex and allowed to bind to the complex, then the excess reagent is washed away. A solution containing the appropriate substrate is then added to the tertiary complex of antibody-antigen-labelled antibody. The substrate reacts with the enzyme linked to the second antibody, giving a qualitative visual signal, which may be further quantitated, usually spectrophotometrically, to give an evaluation of the amount of antigen which is present in the serum sample.

Alternately, fluorescent compounds, such as fluorescein or rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labelled antibody is allowed to bind to the first antigen-complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Alternatively, the sample to be tested, either mammalian blood or other body fluid containing the soluble non-crosslinked fibrin DesAABB polymer and the soluble crosslinked DesAABB fibrin polymer may be used in a single site immunoassay wherein it is adhered to a solid substrate either covalently or noncovalently. An unlabeled antibody is brought into contact with the sample bound on the solid substrate. After a suitable period of incubation, for a period of time sufficient to allow formation of an antibody-antigen binary complex a second antibody, labelled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., zenogeneic antibody to immunoglobulin, particularly anti-(IgM and IgG) linked to a reporter molecule) that is capable of binding an antibody that is specific for the soluble crosslinked fibrin polymer and the soluble non-crosslinked fibrin polymer.

The detection and measurement of soluble non-crosslinked DesAABB fibrin polymers and soluble crosslinked DesAABB fibrin polymers in vitro is particularly useful when such detection and measurement is done, using the plasma of patients, to obtain an indication of an impending or existing thrombotic event, said event being due to an impending or existing thrombosis. See, e.g., W. Nieuwenhuizen, p. 94, Bang and Chang, pp. 109–122, and Marder et al. U.S. Pat. No. 5,206,140. Such events include, for example, deep vein thrombosis ("DVT"), a condition which arises as a result of blood clot formation in the deep veins of the leg; pulmonary embolism (PE), which arises when a thrombus (blood clot) becomes dislodged from the deep veins and embolizes to the pulmonary vasculature; disseminated intravascular coagulation, which arises as a result of systemic activation of the blood clotting cascade (e.g., in bacterial infection); myocardial infarction (MI), which arises as a result of a thrombus occluding the coronary arteries which supply blood to the heart muscle; stroke; and intracardiac thrombi formed as a result of atrial fibrillation. The type of thrombotic event can be diagnosed by use of the assay for detection and measurement of soluble non-crosslinked DesAABB fibrin polymers and soluble crosslinked DesAABB fibrin polymers in combination with observation of other patient symptoms. The symptoms utilized are those which would be commonly utilized in clinical diagnosis of an impending thrombotic event. For example, said detection and measurement of soluble DesAABB fibrin polymers is particularly useful as a means of differentially diagnosing patients with chest pain due to impending MI from patients with chest pain due to other conditions.

6.3 EXAMPLES OF MATERIALS & METHODS

6.3.1. PROTEINS

Bovine Serum Albumin and Thrombin were both purchased from ICN (Costa Mesa, Calif.). Hirudin, horseradish peroxidase and o-phenylenediamine dihydrochloride substrate tablets were all purchased from Sigma Chemical Co. (St. Louis, Mo.). Human fibrinogen (grade L) was purchased from Helena Laboratories (Beaumont, Tex.).

Fibrinogen was further purified by ammonium sulphate precipitation as described by Holm et al., *Thromb. Res*, 37: 165–176 (1985). The anti-fibrin monoclonal antibody, MH1, used in the assay system was produced as described, section 5 above. The antifibrinogen monoclonal antibody, 45J, was produced as described, section 5 above.

DesAABB fibrin monomer was prepared by dissolving non-crosslinked fibrin polymer in a solution of 50 mM sodium acetate buffer (pH 5.3) containing sodium bromideim.

Crosslinked soluble DesAABB fibrin polymers were produced by incubation of fibrinogen or citrated plasma with a low level of thrombin (0.025 units/ml) for 7–8 minutes. The reaction mixture also contained Factor XIIIa. The reaction was quenched by the addition of hirudin to the reaction mixture, (final concentration 10 ATU/ml).

Non-crosslinked soluble DesAABB fibrin polymers were produced by incubating citrated plasma or fibrinogen with a solution of thrombin containing EDTA (12 mM final concentration) for 7–8 minutes at 37° C. The reaction was quenched by the addition of excess hirudin to the reaction mixture, (final concentration 10 ATU/ml).

6.3.2. MH1 AND 45J HORSERADISH PEROXIDASE CONJUGATE (adapted from Wilson and Nakane, Immunofluorescence and Related Staining Techniques, Knapp, et al. (eds), pp. 215–224, Elsevier/North Holland Biomedical Press, Amsterdam (1978))

Horseradish peroxidase (HRP) (RZ>3) (10 mg) was dissolved in 1 ml of distilled water. A freshly prepared solution of 0.1M sodium periodate (0.4 ml) was added and mixed gently for 20 minutes. The solution was then transferred to a sodium acetate buffer (1% mM, pH 4.4) at 4° C. using a Centricon 10 micro-concentrator.

The pH of the solution was raised to 9.5 by adding 40 $\mu$l of 0.2M sodium carbonate-bicarbonate buffer (pH 9.5). MH1 antibody (20 mg) in 2.0 ml of 0.01M sodium carbonate-bicarbonate buffer (pH 9.5) was then added without delay. This solution was mixed gently at room temperature for 2 hours after which 0.2 ml of a freshly prepared sodium borohydride solution (4 mg/ml) was added. The mixture was allowed to stand for 2 hours at 4° C.

Finally the antibody HRP conjugate was dialyzed against 5×4 liters of PBS at 2°–8° C.

The conjugate was stored in a brown container at 2°–8° C.

6.3.3. BLOOD SAMPLES

Blood samples were acquired with consent from both healthy volunteers and from emergency room patients who presented clinical symptoms of MI, e.g., severe chest pain. The blood samples were collected into sodium citrate using vacutainers (Becton Dickinson). Plasma was separated by centrifugation at 2400 RPM for 15 minutes. The plasma was either used immediately or stored frozen at −70° C.

6.3.4. ELISA PROCEDURE FOR MEASURING SOLUBLE FIBRIN

Soluble fibrin was detected in fresh or frozen plasma samples using a sandwich type enzyme-linked immunoassay system. The capture antibody in the current invention was the antifibrin MH1 antibody. The detection (or tag antibody) was a HRP conjugate of the same antibody. Alternatively, a HRP conjugate of the antifibrinogen antibody 45J, could be employed as the tagging antibody.

96 well polyvinyl chloride (PVC) microtitre plates (Costar Cambridge, Mass.) were coated with the monoclonal antibody MH1 by incubation of a 100 $\mu$l solution of the Mab (at 50 $\mu$g/mL) in coating buffer (sodium borate, ph 8.5) for 12–16 hours at 4° C. Unbound antibody was removed from the plates by washing the wells three times with a solution of PBS-TWEEN™ dispersant. The MH1-coated wells were postcoated with BSA by incubating a 200 $\mu$l solution of BSA (1%) in PBS (PBS-BSA) for 1 hour at 37° C. Unbound BSA was removed by inverting the plates and tapping gently onto a paper towel. Citrated samples (50 $\mu$l) containing soluble fibrin were incubated on the MH1-BSA blocked wells for 30 minutes at 37° C. Unbound material was removed by inversion and gentle tapping of the microtitre plates. The wells were then washed three times with a solution of PBS-TWEEN™ dispersant Bound soluble fibrin was detected by first incubating 100 $\mu$l of PBS-BSA solution of the MH1-HRP conjugate (or a HRP conjugate of an antifibrin(ogen) antibody, 45J) in the wells for 30 minutes at 37° C. Unbound conjugate was removed by inverting the plate and washing the wells 3 times with PBS-Tween. The bound conjugate was detected by addition of 100 $\mu$l of O-phenylenediamine dihydrochloride solution for 10 minutes at room temperature. The substrate solution was prepared by dissolving a tablet of O-phenylenediamine dihydrochloride in a sodium citrate solution containing $H_2O_2$.

The colorimetric reaction was quenched after 10 minutes by addition of a 25 $\mu$L solution of $H_2SO_4$ (1M). The absorbance of the solution in each well was determined at 490 nm in a Thermomax microtitre plate reader (Molecular Devices, Menlo Park, Calif.).

6.3.5 PREPARATION OF COLUMNS FOR AFFINITY CHROMATOGRAPHY

SEPHAROSE™ gel MH1 columns were prepared as follows:

1 g of freeze dried cyanogen bromide activated SEPHAROSE™ 4B gel (Pharmacia) was weighed out and suspended in 1 mM HCl. The swollen gel was washed for 15 minutes in 1 mM HCl on a sintered glass filter.

MH1 antibody (20 mg) was dissolved in coupling buffer (0.1M $NaHCO_3$, pH 8.3 containing 0.5M NaCl) and gently mixed with the swollen gel in a stoppered vessel for 2 hours at room temperature or overnight at 4° C.

After mixing, the gel was washed with coupling buffer to remove excess antibody. Unblocked active sites were blocked by treating with 0.1M Tris HCl, pH 8.0 (or 1M ethanolamine, pH 9.0) for 2 hours at room temperature. The antibody-bound gel was then washed 3× with 0.1M Acetate buffer (pH 4.0 containing 0.5M NaCl) followed by Tris buffer (0.1M, pH 8.0 containing NaCl 0.5M). Coupled antibody was stored at 4° C. in sodium azide solution (0.05%).

SEPHAROSE™ gel DesAABB fibrin monomer columns were prepared as follows: DesAABB fibrin monomers were coupled to cyanogen bromide-activated SEPHAROSE™ 4B gel in the presence of 1M NaBr in 0.1M borate buffer (pH 8.2) using the procedure described above for preparation of SEPHAROSE™ gel MH1.

6.3.6 CHARACTERIZATION OF THE SOLUBLE FIBRIN ENTITY RECOGNIZED BY THE IN VITRO ASSAY FOR SOLUBLE FIBRIN POLYMERS USING MH1 TO DETECT SOLUBLE FIBRIN

It has been demonstrated above, Section 5.5, that the MH1 antibody does not recognize fibrinogen, the plasma precursor of the fibrin polymer. It was also shown above, Section 5.5, that the antibody recognizes both crosslinked and non-crosslinked fibrin polymer. In addition, it was shown above, Section 5.5, that plasmin degradation of fibrin, (or any process which leads to the destruction of the fibrin polymeric structure) causes a loss of immune recognition of fibrin by such antibody. Consequently, the MH1 antibody does not recognize any of the known plasmin degradation products of crosslinked fibrin.

Figure 1B:
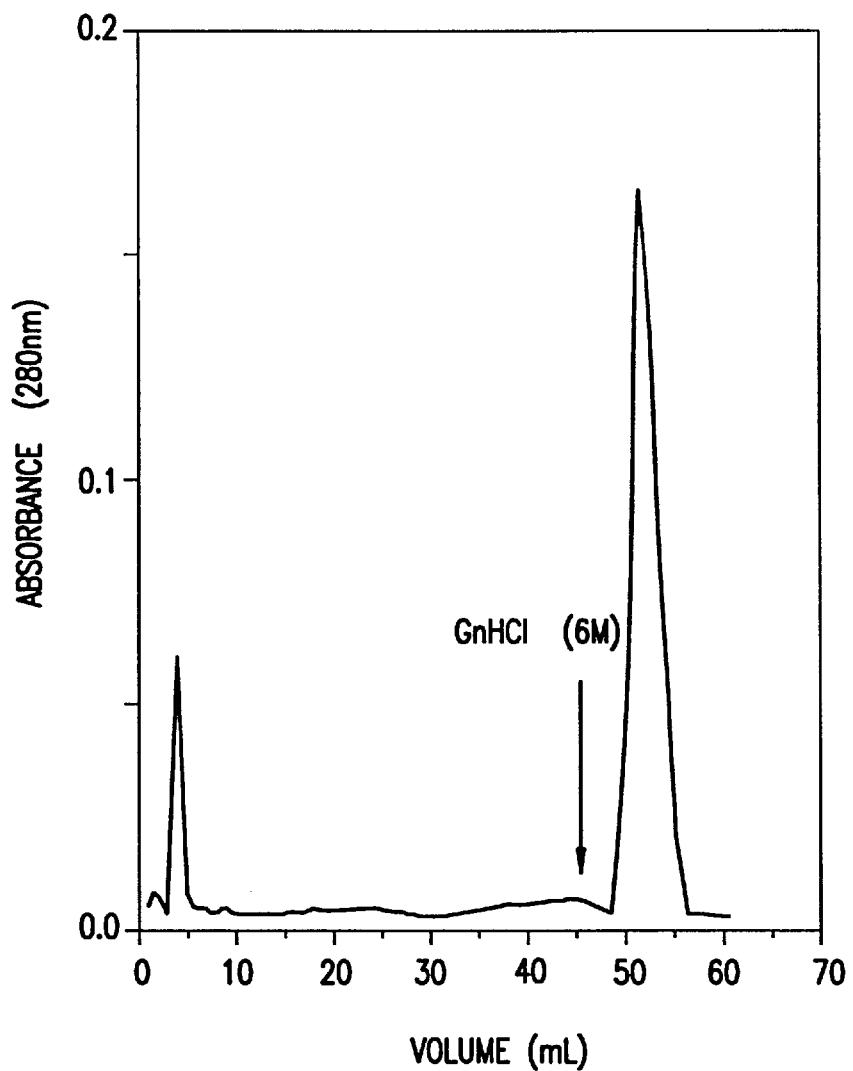
FIG. 1(B) Control experiment to confirm the binding capacity of the SEPHAROSE™ gel DesAABB fibrin monomer matrix using the fibrinogen specific antibody 45J.

Evidence that the MH1 antibody only recognizes the polymeric structure of DesAABB fibrin and does not recognize the monomeric desAABB fibrin entity was obtained by affinity chromatography. Briefly, 0.5 mg of the MH1 antibody was passaged over a 5 ml Sepharose desAABB fibrin monomer column. The column was washed with equilibration buffer (0.1 m Tris buffered saline (TBS), pH 8.5). No significant binding of the antibody to the column was observed. As shown in FIG. 1A, the antibody eluted in the run through of the column. When the column was eluted with 6M guanidine hydrochloride, a small amount of bound protein was recovered. Protein was detected by monitoring all fractions at 280 nm. Antibody was determined by testing immunoreactivity of the protein by means of a solid phase ELISA using fibrin coated microtiter wells. See section 5.4.2 above for description of the ELISA used. The protein bound to the column is a result of the presence of a small amount of contaminating soluble DesAABB fibrin polymer coupled to the DesAABB fibrin monomer column. This contaminant is present in the starting material used in the preparation of the DesAABB fibrin monomer column. To demonstrate that the SEPHAROSE™ gel desAABB fibrin monomer column was capable of binding an antibody, a fibrinogen specific monoclonal antibody (Mab) was passaged over the column in a control experiment. As shown in FIG. 1B, the column bound the control Mab, the antifibrinogen antibody 45J, and treatment with guanidine hydrochloride (6M) was required to elute the 45J antibody.

Figure 2:
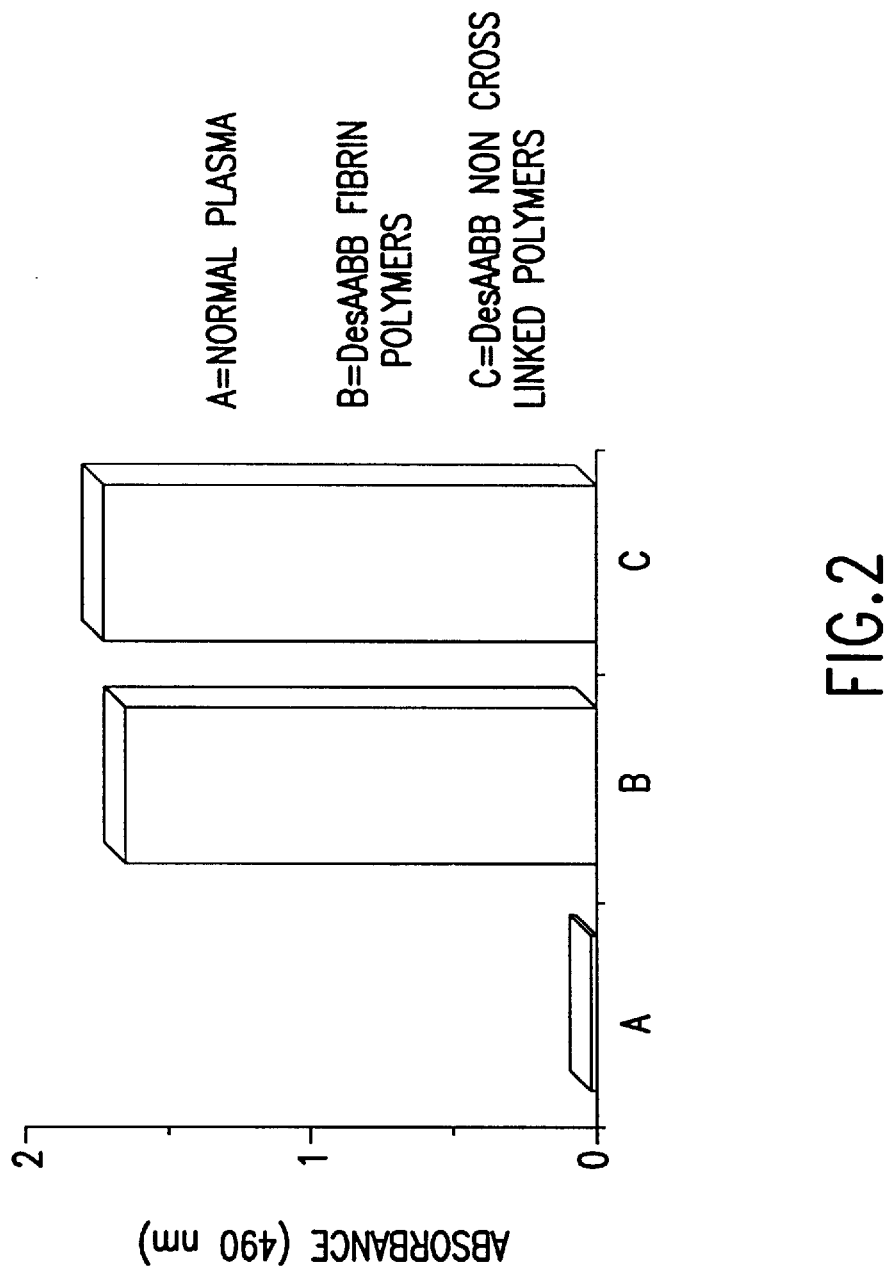
FIG. 2 Immunoreactivity of non-crosslinked DesAABB fibrin polymers and crosslinked DesAABB fibrin polymers in the in vitro assay for soluble DesAABB fibrin polymers using MH1.

Evidence that the MH1 antibody, described above, recognizes both crosslinked and non-crosslinked soluble DesAABB fibrin polymers was obtained in an experiment in which soluble DesAABB fibrin polymers were generated by addition of thrombin to citrated plasma samples in the presence and absence of EDTA (EDTA prevents factor XIIIa from crosslinking DesAABB fibrin polymers). The crosslinked and non-crosslinked soluble DesAABB fibrin polymers were prepared as described in section 6.3.1 and their respective immunoreactivities were measured using the ELISA as described in section 6.3.4. As shown in FIG. 2, there is no significant difference in the immunoreactivity of crosslinked (B) and non-crosslinked (C) fibrin polymers in the assay system.

Figure 3:
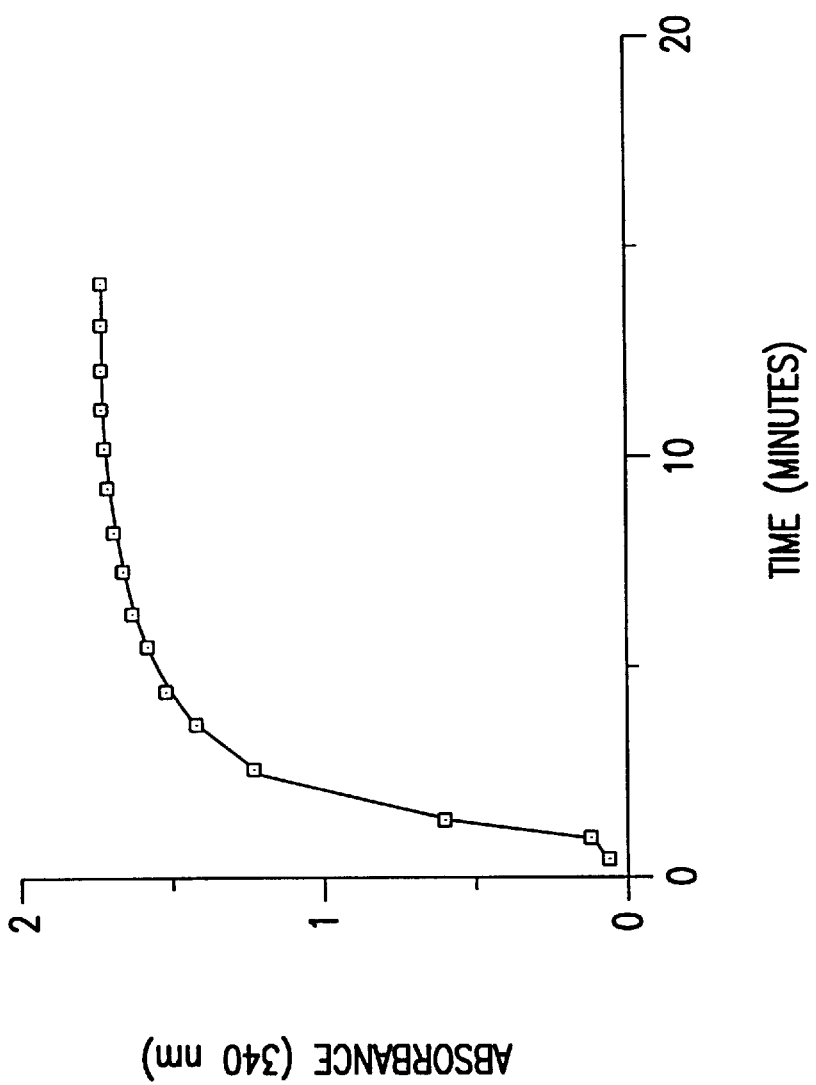
FIG. 3 The formation of DesAA fibrin by batroxobin treatment of plasma fibrinogen.
Figure 4:
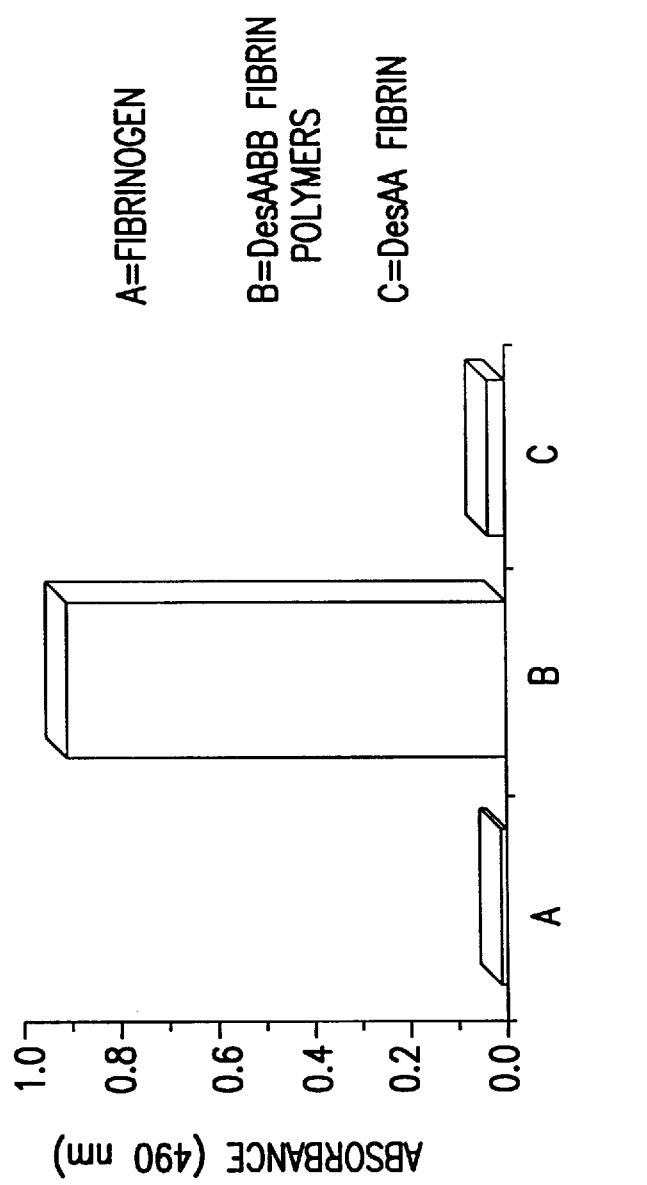
FIG. 4 Immunoreactivity of soluble DesAA fibrin polymers in the in vitro assay system for soluble DesAABB fibrin polymers using MH1.

Evidence that the MH1 antibody does not recognize soluble desAA fibrin polymer was obtained in an experiment wherein DesAA fibrin polymer was prepared by treating fibrinogen or plasma with the snake venom derived enzyme Batroxobin, from Bothrops atrox, which selectively cleaves fibrinopeptide A (FPA) from the fibrinogen molecule. Batroxobin does not cleave fibrinopeptide B (FPB), in contrast to thrombin which cleaves both FPA and FPB. The removal of FPA results in polymerization of the desAA fibrin monomer units and the formation of a DesAA fibrin clot. FIG. 3 demonstrates clot formation, as measured by absorbance of the reaction mixture at 340 nm, when a batroxobin solution is incubated for 15 minutes at room treatment with a fibrinogen sample. The absorbance increases gradually with time as the soluble DesAA fibrin polymers increase in length and concentration, until finally the clot is formed. In the experiment to test MH1 assay recognition of desAA fibrin, soluble desAA fibrin polymer was generated in vitro by incubation of a fibrinogen sample with batroxobin (final concentration, 0.5 units/mL) at 37° C. An aliquot was removed from the batroxobin treated sample after 7 minutes and tested in the ELISA assay of section 6.3.4. No reactivity was demonstrated with this sample, sample C, as shown in FIG. 4. It can also be deduced from this experiment that the assay system does not recognize fibrinogen-desAA fibrin complex which is another source of soluble fibrin. Clearly the reaction mixture produced in this experiment would contain such "soluble fibrin" entities since the batroxobin produces desAA fibrin monomers which are free to interact with other desAA monomers or non-digested fibrinogen molecules. Since no reaction was demonstrated in the assay system after addition of batroxobin, the conclusion can be drawn that the assay does not detect these fibrinogen-desAA fibrin entities. Sample B, which is the positive control, was composed of DesAABB fibrin polymers formed by treatment of a plasma sample with thrombin and hirudin. Untreated fibrinogen, sample A, was added as a negative control.

Figure 5:
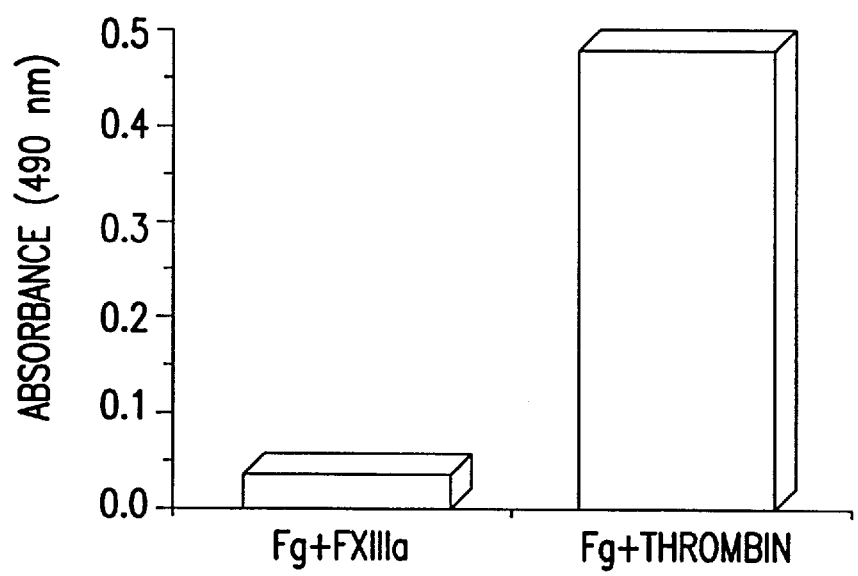
FIG. 5 Immunoreactivity of MH1 antibody with activated Factor XIII (Factor XIIIa)—treated fibrinogen.

Soluble fibrin complex can also arise due to factor XIIIa crosslinking of native fibrinogen molecules to form fibrinogen dimers (Kanaide et al., *J. Lab. Clin. Med.* 86: 574–579 (1975)) Factor XIIIa (FXIIIa) treated fibrinogen is not detected by the assay system. In this experiment, fibrinogen coated microtiter plates were first treated with thrombin-activated factor XIIIa for 1½ hours at 37° C. After quenching residual thrombin activity, the MH1 antibody was incubated in the FXIIIa treated wells and bound MH1 was detected by use of anti-mouse alkaline phosphatase conjugate. Bound anti-mouse antibody was detected by the addition of an alkaline phosphatase substrate. The level of MH2 bound to the wells was measured by reading the optical density at 490 nm. FIG. 5, sample labeled Fg+FXIIa shows that no MH1 was bound to the wells, indicating that the antibody does not recognize crosslinked fibrinogen structures. As a positive control the fibrinogen coated wells were treated with thrombin to produce desAABB fibrin polymers and tested for immunoreactivity with MH1 antibody, FIG. 5, sample labeled Fg+Thrombin.

6.3.7 MEASUREMENT OF SOLUBLE DESAABB FIBRIN POLYMER FORMATION IN VITRO

Soluble DesAABB fibrin polymers were produced in vitro by addition of low levels of thrombin (0.025 NIH units/mL) to a citrated plasma sample. The sample was incubated at 37° C. Aliquots were removed from the sample at 1 minute intervals and the thrombin activity was quenched by the addition of the potent thrombin inhibitor, hirudin (final concentration 2-ATU/ml). The amount of soluble DesAABB fibrin polymer in each aliquot was measured by the ELISA procedure described in section 6.3.4.

Figure 6:
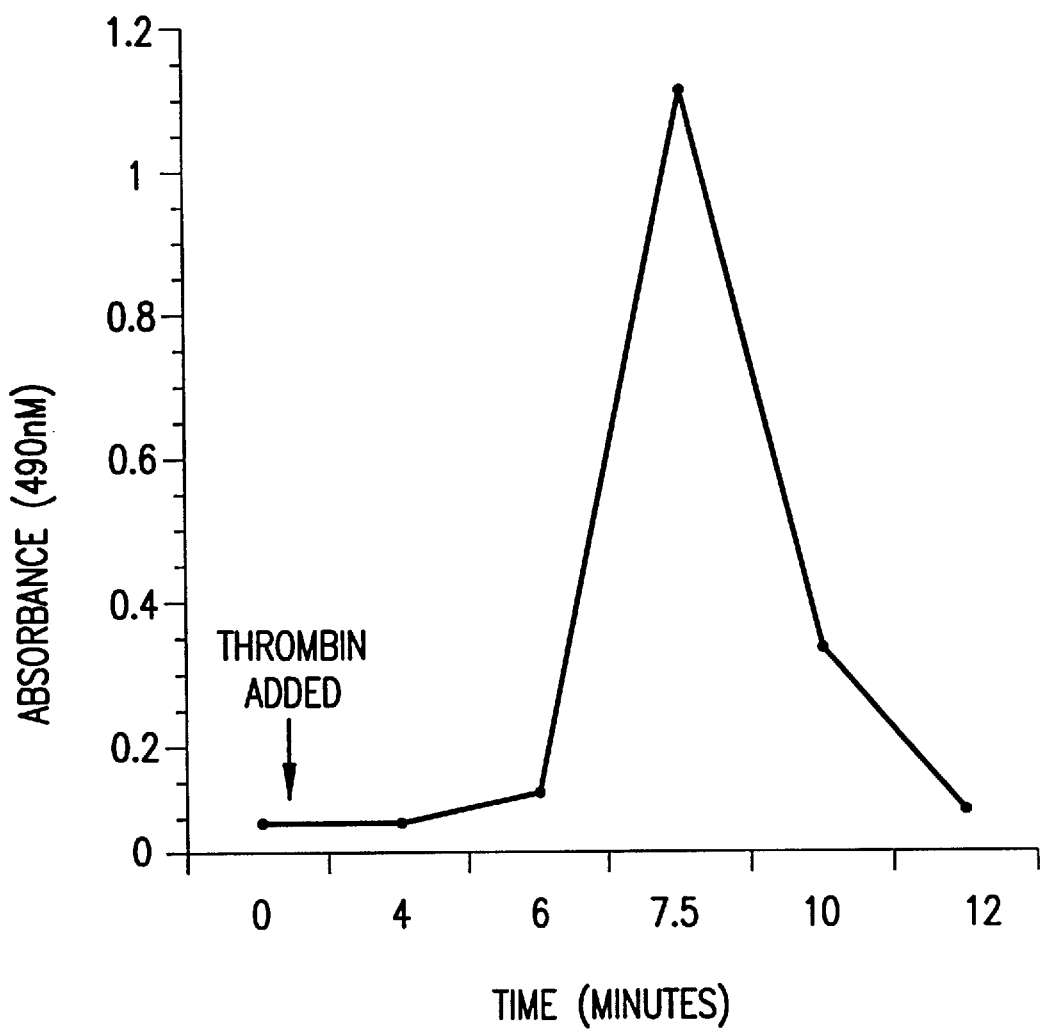
FIG. 6 Measurement of soluble DesAABB fibrin polymer formation in vitro using the soluble fibrin MH1 assay.

As shown in FIG. 6, the amount of soluble fibrin polymer, indicated by the absorbance at 490 nm, rises sharply after an initial lag period of 4–5 minutes after the addition of thrombin to the plasma. The level of soluble fibrin polymers peaks at approximately 7.5 minutes after the addition of thrombin to the plasma. The steep decrease in the soluble fibrin level observed after 9–10 minutes coincides with gelation and formation of insoluble fibrin polymers (clot formation).

6.3.8 PURIFICATION OF SOLUBLE FIBRIN POLYMERS FROM PLASMA BY SEPHAROSE™ GEL-MH1 AFFINITY CHROMATOGRAPHY

Figure 7:
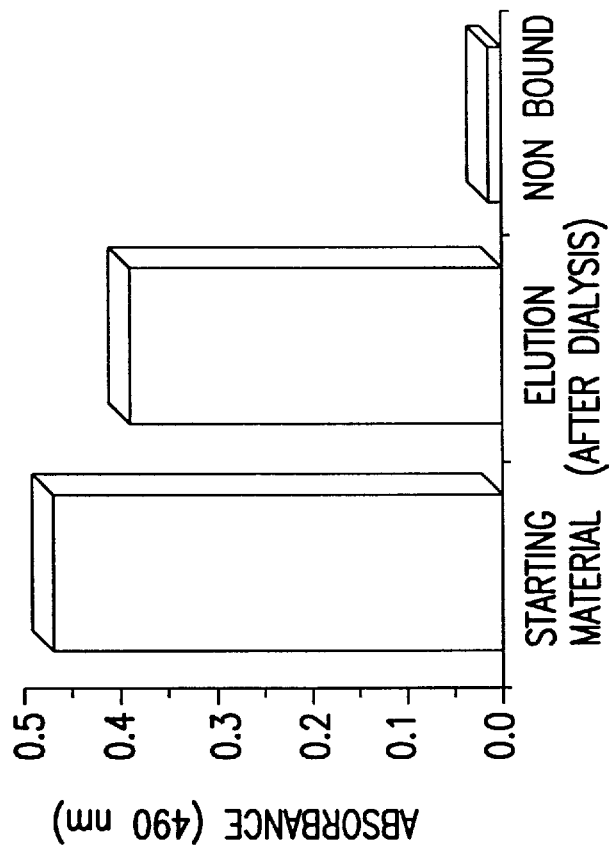
FIG. 7 Demonstration of the purification of soluble fibrin from plasma by utilization of a SEPHAROSE™ gel MH1 column.

A plasma sample was incubated with thrombin (0.025 units ml) for 7 minutes at 37° C. The thrombin activity was quenched by the addition of excess hirudin. The reaction mixture was passaged over a SEPHAROSE™ gel-MH1 column. The starting material, the run through (nonbound material) and the bound protein (purified protein) which protein was eluted using NaSCN (3M) and dialyzed against PBS, were tested for immunoreactivity with MH1 using the ELISA assay of section 6.3.4. The immunoreactivity of the thrombin treated plasma after quenching with hirudin (Starting Material), of the bound protein after removal from the column and dialysis (Elution), and of the nonbound material (Nonbound) is shown in FIG. 7. The starting material and the bound protein after dialysis were immunoreactive with MH1 while the nonbound material was not.

Figure 8:
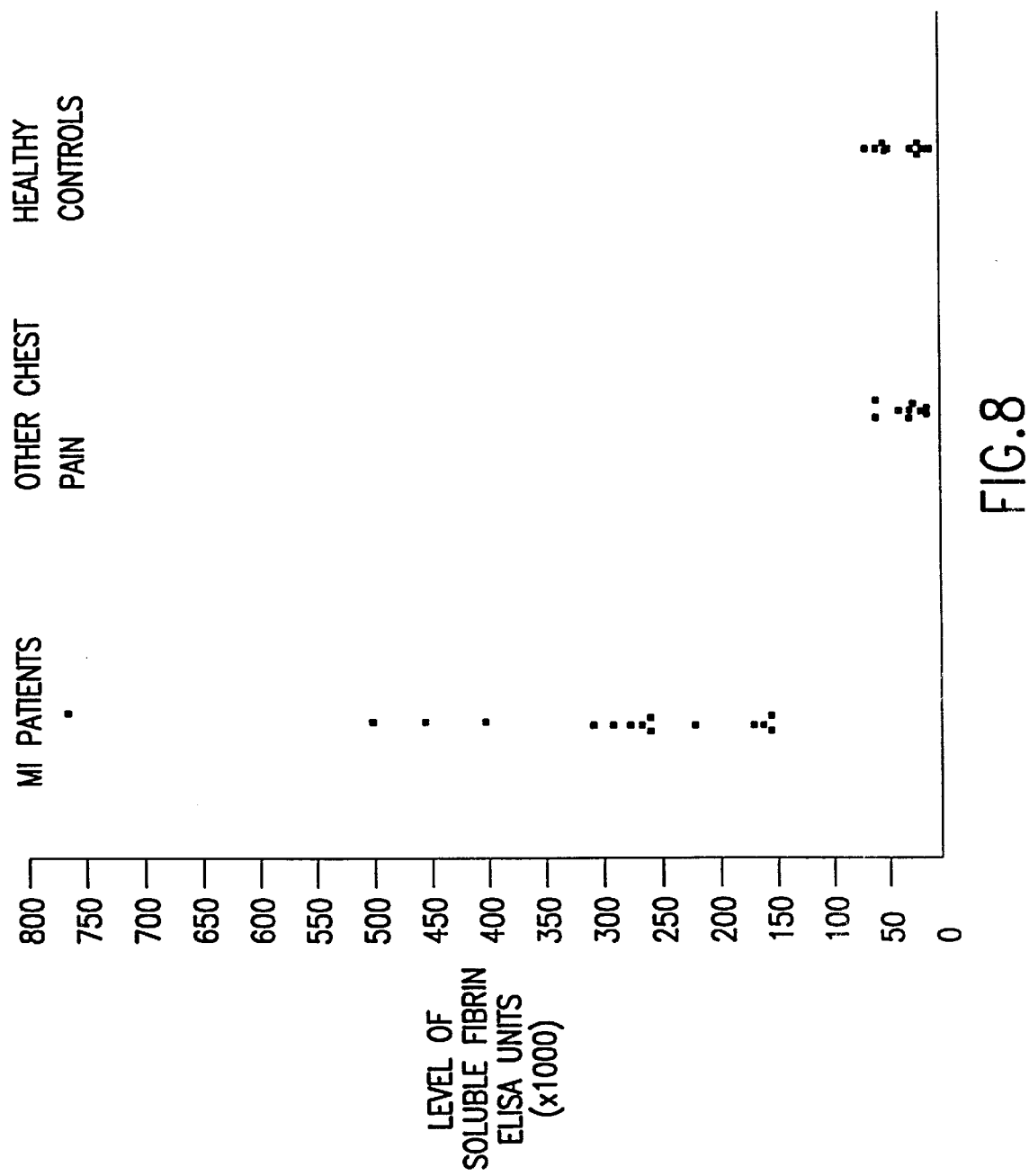
FIG. 8 Measurement of soluble DesAABB fibrin polymers in the blood of patients with chest pain and confirmed myocardial infarction.

6.3.9 IN VITRO DETECTION AND MEASUREMENT OF SOLUBLE CROSSLINKED AND SOLUBLE NON-CROSSLINKED FIBRIN POLYMERS FOR DIAGNOSIS OF MI 36 different plasma samples were tested for soluble crosslinked and soluble non-crosslinked DesAABB fibrin polymer levels using the ELISA assay described above in section 6.3.4 with MH1 as the capture antibody. After collection, plasma samples were drawn into anticoagulant and frozen. The thawed samples were tested for soluble crosslinked and non-crosslinked DesAABB fibrin polymer. Ten of these 36 samples were taken from healthy control humans. Healthy controls were recruited from laboratory personnel who were in excellent health and who did not experience chest pain even after exertion. All other samples were from patients at the emergency room facility of a local community hospital. All emergency room patients had clinical symptoms (chest pain) suggestive of myocardial infarction (MI); 15 were confirmed as suffering from MI; the other 11 patients were all confirmed not to be suffering from MI. The latter patient group was diagnosed with various clinical conditions including, angina pectoris, anxiety, pulmonary edema. The blood samples were drawn from patients immediately after their admission to the emergency room. In most cases information on the duration of the symptoms were recorded. In this study all patients had been experiencing chest pain for 1–3 hours prior to admission. As shown in FIG. 8, in all cases the patients with confirmed MI had significantly higher levels of soluble DesAABB fibrin polymers than the healthy controls (3–30 fold difference). In those patients with chest pain but without MI, the levels of soluble DesAABB fibrin polymers were not significantly different from those of the healthy controls. (Levels of soluble crosslinked and soluble non-crosslinked DesAABB fibrin polymers are shown as "Level of Soluble Fibrin Elisa Units (×1000)").

The sensitivity of this assay system was therefore 100% (for n=36) and the specificity was also 100% (for n=36) i.e., there were no false positives and no false negatives. It can therefore be concluded that this assay system has a high level of diagnostic accuracy for myocardial infarction.

6.4 KITS FOR IN VITRO DETECTION OF SOLUBLE CROSSLINKED FIBRIN POLYMERS AND SOLUBLE NON-CROSSLINKED FIBRIN POLYMERS

It is to be understood that the present invention is not limited to the use of monoclonal antibodies in the assay. However, where such antibody is used, with respect to the kit hereinafter described, these kits contain a set of standards, a first antibody (i.e., capture antibody, for example MH1) which can be immobilized on a surface and a second antibody labeled with a signal generator as described above. These kits contain standards in the form of known amounts of soluble cross-linked DesAABB fibrin polymer and soluble non-crosslinked DesAABB fibrin polymer. Such standards may be prepared by the isolation of soluble crosslinked and soluble non-crosslinked DesAABB fibrin polymers using the MH1 SEPHAROSE™ gel affinity column as described above. The kits may also contain specific buffers, separating agents and controls. The kits may contain collection devices or chemicals to treat the sample to be assayed.

All publications and patents cited above are herein incorporated by reference.

I claim:

1. A method for the in vitro detection of the presence or amount of soluble crosslinked DesAABB fibrin polymers and soluble non-crosslinked DesAABB fibrin polymers in a mammalian sample, which comprises contacting the sample with monoclonal antibody MH1 produced by hybridoma ATCC HB 9739, or an antibody that binds to the same epitope as monoclonal antibody MH1, or an immunoreactive fragment thereof to form an immunocomplex therewith and detecting the presence or amount of said immunocomplex, thereby detecting the presence or amount of said soluble crosslinked DesAABB fibrin polymers and said soluble non-crosslinked DesAABB fibrin polymers in said sample.

2. The method of claim 1, in which the antibody is MH1 or a single chain antibody of MH1 or a Fab fragment of MH1.

3. The method of claim 1, wherein the mammalian sample is a human sample.

4. The method of claim 3, wherein the human sample is a body fluid.

5. The method of claim 4, wherein the body fluid is blood.

6. The method of claim 1, in which the immunocomplex is detected or quantified using a secondary antibody or an immunoreactive fragment thereof that specifically binds to said immunocomplex, in which said secondary antibody or immunoreactive fragment is labelled with a reporter molecule that produces a detectable signal that is measured and that correlates to the presence or amount of said immunocomplex.

7. The method of claim 1, in which the secondary antibody is monoclonal antibody 45J produced by hybridoma ATCC HB 9740, or an antibody that binds to the same epitope as monoclonal antibody 45J, or an immunoreactive fragment thereof.

8. The method of claim 7, in which the secondary antibody is monoclonal antibody 45J or a single chain antibody of 45J or a Fab fragment of 45J.

9. A method for evaluating predisposition for thrombus formation, for supporting a diagnosis of an occurrence of a thrombus, or for monitoring the formation of a thrombus in a mammal, comprising detecting the amount of soluble crosslinked DesAABB fibrin polymers and soluble non-crosslinked DesAABB fibrin polymers in a sample from said mammal, comprising contacting said sample with monoclonal antibody MH1 produced by hybridoma ATCC HB 9739, or an antibody that binds to the same epitope as monoclonal antibody MH1, or an immunoreactive fragment thereof, to form an immunocomplex therewith, detecting the amount of said immunocomplex, and comparing said amount to a control sample, to evaluate the predisposition for a thrombus formation, or the occurrence of a thrombus, or to monitor the formation of a thrombus in the mammal.

10. The method of claim 9, in which the antibody is MH1 or a single chain antibody of MH1 or a Fab fragment of MH1.

11. The method of claim 9, wherein the mammal has a disease selected from the group consisting of myocardial infarction, deep vein thrombosis, pulmonary embolism, disseminated intravascular coagulation, stroke, and intracardiac thrombus formed as a result of atrial fibrillation.

12. The method of claim 9, wherein the mammalian sample is a human sample.

13. The method of claim 12, wherein the human sample is a body fluid.

14. The method of claim 13, wherein the body fluid is blood.

15. The method of claim 9, in which the amount of immunocomplex is detected using a secondary antibody or immunoreactive fragment thereof which specifically binds to the immunocomplex, in which the secondary antibody or immunoreactive fragment is labelled with a reporter molecule that produces a detectable signal that is measured and that correlates to the amount of the immunocomplex.

16. The method of claim 15, in which the secondary antibody is monoclonal antibody 45J produced by hybridoma ATCC HB 9740, or an antibody that binds to the same epitope as monoclonal antibody 45J, or an immunoreactive fragment thereof.

17. The method of claim 16, in which the secondary antibody is monoclonal antibody 45J or a single chain antibody of 45J or a Fab fragment of 45J.

18. A kit for detecting in vitro the presence or amount of soluble crosslinked DesAABB fibrin polymers and soluble non-crosslinked DesAABB fibrin polymers in a sample from a mammal, which comprises:

(a) measured amounts of standards containing said soluble crosslinked DesAABB fibrin polymers and said soluble non-crosslinked DesAABB fibrin polymers;

(b) means for forming an immunocomplex with said soluble crosslinked DesAABB fibrin polymers and said soluble non-crosslinked DesAABB fibrin polymers, said means comprising monoclonal antibody MH1 produced by hybridoma ATCC HB 9739, or an antibody that binds to the same epitope as monoclonal antibody MH1, or an immunoreactive fragment thereof; and (c) means for detecting the amount of said immunocomplex.

19. The kit of claim 18, in which the means for forming an immunocomplex with said soluble crosslinked DesAABB fibrin polymers and said soluble non-crosslinked DesAABB fibrin polymers is monoclonal antibody MH1 or a single chain ab of MH1 or a Fab fragment of MH1.

20. The kit of claim 18, in which the means for detecting the amount of said immunocomplex is a secondary antibody or immunoreactive fragment thereof labelled with a reporter molecule that produces a detectable signal that is measured and that correlates to the amount of said immunocomplex.

21. The kit of claim 20, in which the secondary antibody monoclonal antibody 45J produced by hybridoma ATCC HB 9740, or an antibody that binds to the same epitope as monoclonal antibody 45J.

22. The kit of claim 21, in which the secondary antibody is monoclonal antibody 45J or a single chain ab of 45J or a Fab fragment of 45J.

* * * * *

UNITED STATES PATENT AND TRADEMARK OFFICE
CERTIFICATE OF CORRECTION

PATENT NO. : 5,843,690
DATED : December 1, 1998
INVENTOR(S) : Paul E. Gargan

It is certified that error appears in the above-identified patent and that said Letters Patent is hereby corrected as shown below:

Column 3, line 42, after "(1974)" insert --,--.

Column 23, line 37, after "80" insert --dispersant--; and line 37-38, after "PBS-" delete "dispersant TWEEN" and insert --TWEEN™ dispersant--.

Column 26, line 23, delete "Table 8" and insert in its place --Table 10--.

Column 26, line 54, delete "125I-" and insert --$^{125}$I--.

Column 38, line 19, delete "PBS-Tween" and insert --a solution of PBS-TWEEN™ dispersant--.

Column 39, at line 56, delete "Bothrops atrox" and insert --*Bothrops atrox*--

Signed and Sealed this

Sixth Day of July, 1999

Q. TODD DICKINSON

*Attest:*

*Attesting Officer*   Acting Commissioner of Patents and Trademarks